(12) United States Patent
Hanuka et al.

(10) Patent No.: US 9,314,365 B2
(45) Date of Patent: Apr. 19, 2016

(54) OSTOMY PORT GAS RELEASE MECHANISM

(71) Applicant: B. Braun Medical SAS, Boulogne-Billancourt (FR)

(72) Inventors: David Hanuka, Ramat-Yishai (IL); Meir Or, Kfar Eschchar (IL)

(73) Assignee: B. Braun Medical SAS, Boulogne-Billancourt (FR)

( * ) Notice: Subject to any disclaimer, the term of this patent is extended or adjusted under 35 U.S.C. 154(b) by 0 days.

(21) Appl. No.: 13/666,244

(22) Filed: Nov. 1, 2012

(65) Prior Publication Data
US 2013/0116642 A1 May 9, 2013

Related U.S. Application Data

(63) Continuation of application No. PCT/IB2011/051932, filed on May 2, 2011, and a continuation-in-part of application No. PCT/IL2010/000565, filed on Jul. 14, 2010.

(60) Provisional application No. 61/431,084, filed on Jan. 10, 2011, provisional application No. 61/225,546, filed on Jul. 14, 2009, provisional application No. 61/330,359, filed on May 2, 2010.

(51) Int. Cl.
| | |
|---|---|
| A61F 5/441 | (2006.01) |
| A61F 5/445 | (2006.01) |
| A61F 5/44 | (2006.01) |
| A61F 5/443 | (2006.01) |
| A61F 5/442 | (2006.01) |
| A61F 5/449 | (2006.01) |

(52) U.S. Cl.
CPC .......... *A61F 5/4407* (2013.01); *A61F 5/44* (2013.01); *A61F 5/441* (2013.01); *A61F 5/442* (2013.01); *A61F 5/443* (2013.01); *A61F 5/4404* (2013.01); *A61F 5/4405* (2013.01); *A61F 5/445* (2013.01); *A61F 5/449* (2013.01); *A61F 2005/4402* (2013.01); *A61F 2005/4455* (2013.01)

(58) Field of Classification Search
USPC .......................................................... 604/333
See application file for complete search history.

(56) References Cited

U.S. PATENT DOCUMENTS

| | | | |
|---|---|---|---|
| 2,243,529 | A | 5/1941 | Grossman et al. |
| 2,341,984 | A | 2/1944 | Graves |

(Continued)

FOREIGN PATENT DOCUMENTS

| | | |
|---|---|---|
| CN | 1694661 | 11/2005 |
| DE | 19921555 | 2/2000 |

(Continued)

OTHER PUBLICATIONS

Communication Relating to the Results of the Partial International Search Dated Sep. 16, 2013 From the International Searching Authority Re. Application No. PCT/IL2013/050401.

(Continued)

*Primary Examiner* — Tatyana Zalukaeva
*Assistant Examiner* — Guy K Townsend
(74) *Attorney, Agent, or Firm* — Kristina Bieker-Brady; Clark & Elbing LLP

(57) ABSTRACT

Controlled or automatic release of gas from ostomy ports. In some embodiments a gap is selectively formed between a cap and a body of an ostomy port. In some embodiments, a dedicated gas exhaust lumen is provided as part of the port. Optionally, the gas release uses a filter to reduce odor.

50 Claims, 11 Drawing Sheets

(56) References Cited

U.S. PATENT DOCUMENTS

| | | | |
|---|---|---|---|
| 2,510,766 A | 6/1950 | Surface |
| 2,544,579 A | 3/1951 | Ardner |
| 2,639,710 A | 5/1953 | Fazio |
| 2,667,167 A | 1/1954 | Raiche |
| 2,971,510 A | 2/1961 | Berger |
| 3,398,744 A | 8/1968 | Hooper |
| 3,447,533 A | 6/1969 | Spicer |
| 3,718,141 A | 2/1973 | Goetz |
| 3,976,076 A | 8/1976 | Beach |
| 4,030,500 A | 6/1977 | Ronnquist |
| 4,121,589 A | 10/1978 | McDonnell |
| 4,170,231 A | 10/1979 | Collins |
| 4,183,357 A | 1/1980 | Bentley et al. |
| 4,209,010 A | 6/1980 | Ward et al. |
| 4,210,131 A | 7/1980 | Perlin |
| 4,211,224 A | 7/1980 | Kubach et al. |
| 4,232,672 A | 11/1980 | Steer et al. |
| 4,265,244 A | 5/1981 | Hill |
| 4,338,937 A | 7/1982 | Lerman |
| 4,344,434 A | 8/1982 | Robertson |
| 4,351,322 A | 9/1982 | Prager |
| 4,381,765 A | 5/1983 | Burton |
| 4,399,809 A | 8/1983 | Baro et al. |
| 4,421,124 A | 12/1983 | Marshall |
| 4,460,363 A | 7/1984 | Steer et al. |
| 4,462,510 A | 7/1984 | Steer et al. |
| 4,516,974 A | 5/1985 | Davis |
| 4,534,761 A | 8/1985 | Raible |
| 4,634,421 A | 1/1987 | Hegemann |
| 4,642,107 A | 2/1987 | Arnone et al. |
| 4,662,890 A | 5/1987 | Burton et al. |
| 4,721,508 A | 1/1988 | Burton |
| 4,786,283 A | 11/1988 | Andersson |
| 4,804,375 A | 2/1989 | Robertson |
| 4,810,250 A | 3/1989 | Ellenberg et al. |
| 4,854,316 A | 8/1989 | Davis |
| 4,863,447 A | 9/1989 | Smith |
| 4,941,869 A | 7/1990 | D'Amico |
| 4,950,223 A | 8/1990 | Silvanov |
| 4,981,465 A | 1/1991 | Ballan et al. |
| 5,004,464 A | 4/1991 | Leise, Jr. |
| 5,026,360 A | 6/1991 | Johnson et al. |
| 5,045,052 A | 9/1991 | Sans |
| 5,108,430 A | 4/1992 | Ravo |
| 5,125,916 A | 6/1992 | Panebianco et al. |
| 5,135,519 A | 8/1992 | Helmer |
| 5,163,897 A | 11/1992 | Persky |
| 5,163,930 A | 11/1992 | Blum |
| 5,261,898 A | 11/1993 | Polin et al. |
| 5,269,774 A | 12/1993 | Gray |
| 5,372,594 A | 12/1994 | Colacello et al. |
| 5,401,264 A | 3/1995 | Leise, Jr. |
| 5,501,678 A | 3/1996 | Olsen |
| 5,549,588 A | 8/1996 | Johnson |
| 5,569,216 A | 10/1996 | Kim |
| 5,658,266 A * | 8/1997 | Colacello | A61F 5/441 604/277 |
| 5,658,267 A | 8/1997 | Colacello et al. |
| 5,683,372 A * | 11/1997 | Colacello | A61F 5/441 604/277 |
| 5,771,590 A * | 6/1998 | Colacello | A61F 5/441 30/360 |
| 5,785,677 A | 7/1998 | Auweiler |
| 5,785,695 A | 7/1998 | Sato et al. |
| 5,947,942 A | 9/1999 | Galjour |
| 6,033,390 A | 3/2000 | Von Dyck |
| 6,050,982 A | 4/2000 | Wheeler |
| 6,329,465 B1 | 12/2001 | Takahashi et al. |
| 6,350,255 B1 | 2/2002 | Von Dyck |
| 6,357,445 B1 | 3/2002 | Shaw |
| 6,481,589 B2 | 11/2002 | Blomdahl et al. |
| 6,485,476 B1 | 11/2002 | Von Dyck et al. |
| 6,595,971 B1 | 7/2003 | Von Dyck et al. |
| 6,659,988 B1 | 12/2003 | Steer et al. |
| 6,689,111 B2 | 2/2004 | Mulhauser et al. |
| 6,695,825 B2 | 2/2004 | Castles |
| 6,723,079 B2 | 4/2004 | Cline |
| 6,963,772 B2 | 11/2005 | Bloom et al. |
| 7,001,367 B2 | 2/2006 | Arkinstall |
| 7,083,569 B2 | 8/2006 | Boulanger et al. |
| 7,087,041 B2 | 8/2006 | Von Dyck et al. |
| 7,250,040 B2 | 7/2007 | Andersen |
| 7,314,443 B2 | 1/2008 | Jordan et al. |
| 7,582,072 B2 | 9/2009 | McMichael |
| 7,670,289 B1 | 3/2010 | McCall |
| 7,857,796 B2 | 12/2010 | Cline et al. |
| 8,070,737 B2 | 12/2011 | Cline et al. |
| 8,092,437 B2 | 1/2012 | Cline |
| 8,100,875 B2 | 1/2012 | Cline et al. |
| 8,142,406 B2 | 3/2012 | Blum |
| 8,388,586 B2 | 3/2013 | Weig |
| 8,460,259 B2 | 6/2013 | Tsai |
| 8,821,464 B2 | 9/2014 | Hanuka et al. |
| 8,821,465 B2 | 9/2014 | Hanuka et al. |
| 8,845,607 B2 | 9/2014 | Hanuka et al. |
| 8,858,519 B2 | 10/2014 | Hanuka et al. |
| 8,864,729 B2 | 10/2014 | Hanuka et al. |
| 8,900,116 B2 | 12/2014 | Hanuka et al. |
| 8,998,862 B2 | 4/2015 | Hanuka et al. |
| 2003/0150050 A1 | 8/2003 | Tanaka et al. |
| 2003/0199783 A1 | 10/2003 | Bloom et al. |
| 2003/0220621 A1 | 11/2003 | Arkinstall |
| 2004/0029467 A1 | 2/2004 | Lacroix |
| 2004/0073179 A1 | 4/2004 | Andersen |
| 2004/0122527 A1 | 6/2004 | Imran |
| 2004/0167376 A1 | 8/2004 | Peters et al. |
| 2004/0171999 A1 | 9/2004 | Andersen et al. |
| 2004/0181197 A1 | 9/2004 | Cline |
| 2005/0027159 A1 | 2/2005 | Feng et al. |
| 2005/0054996 A1 | 3/2005 | Gregory |
| 2005/0065488 A1 | 3/2005 | Elliott |
| 2005/0104457 A1 | 5/2005 | Jordan et al. |
| 2006/0048283 A1 | 3/2006 | Sorensen |
| 2006/0106354 A1 | 5/2006 | Vantroostenberghe |
| 2006/0206069 A1 | 9/2006 | Cline |
| 2006/0229596 A1 | 10/2006 | Weiser et al. |
| 2007/0049878 A1 | 3/2007 | Kim et al. |
| 2007/0088300 A1 | 4/2007 | Cline et al. |
| 2007/0129695 A1 | 6/2007 | Blum |
| 2007/0142780 A1 * | 6/2007 | Van Lue | A61B 17/3462 604/167.01 |
| 2007/0191794 A1 | 8/2007 | Cline et al. |
| 2007/0219532 A1 | 9/2007 | Karpowicz et al. |
| 2007/0260206 A1 | 11/2007 | Mullejans et al. |
| 2007/0276346 A1 | 11/2007 | Poulsen et al. |
| 2008/0004580 A1 | 1/2008 | Mullejans et al. |
| 2008/0033380 A1 | 2/2008 | Andersen |
| 2008/0091154 A1 | 4/2008 | Botten |
| 2008/0108862 A1 | 5/2008 | Jordan et al. |
| 2008/0135044 A1 | 6/2008 | Freitag et al. |
| 2008/0269698 A1 | 10/2008 | Alexander et al. |
| 2008/0275410 A1 * | 11/2008 | Burt | A61F 5/4405 604/333 |
| 2009/0043151 A1 | 2/2009 | Gobel |
| 2009/0216206 A1 | 8/2009 | Nishtala et al. |
| 2009/0247969 A1 | 10/2009 | Nishtala et al. |
| 2010/0069859 A1 | 3/2010 | Weig |
| 2010/0174253 A1 | 7/2010 | Cline et al. |
| 2011/0015475 A1 | 1/2011 | Hanuka et al. |
| 2011/0040231 A1 | 2/2011 | Gregory |
| 2011/0106032 A1 | 5/2011 | Kratky |
| 2012/0136324 A1 | 5/2012 | Hanuka et al. |
| 2013/0053803 A1 | 2/2013 | Willoughby et al. |
| 2013/0060212 A1 | 3/2013 | Hanuka et al. |
| 2013/0060213 A1 | 3/2013 | Hanuka et al. |
| 2013/0060214 A1 | 3/2013 | Willoughby et al. |
| 2013/0079736 A1 | 3/2013 | Hanuka et al. |
| 2013/0079737 A1 | 3/2013 | Hanuka et al. |
| 2013/0079738 A1 | 3/2013 | Hanuka et al. |
| 2013/0304008 A1 | 11/2013 | Hanuka et al. |
| 2015/0025488 A1 | 1/2015 | Hanuka et al. |
| 2015/0057626 A1 | 2/2015 | Hanuka et al. |
| 2015/0141944 A1 | 5/2015 | Hanuka et al. |
| 2015/0305916 A1 | 10/2015 | Hanuka et al. |

(56) References Cited

U.S. PATENT DOCUMENTS

FOREIGN PATENT DOCUMENTS

| | | |
|---|---|---|
| DE | 102004001631 | 8/2004 |
| DE | 102007062133 | 7/2009 |
| EP | 1795157 | 6/2007 |
| EP | 2027835 | 2/2009 |
| FR | 2870112 | 11/2005 |
| GB | 2094153 | 9/1982 |
| JP | 2006-314479 | 11/2006 |
| JP | 2008-507308 | 3/2008 |
| WO | WO 87/03192 | 6/1987 |
| WO | WO 90/07311 | 7/1990 |
| WO | WO 96/32904 | 10/1996 |
| WO | WO 99/43277 | 9/1999 |
| WO | WO 01/49224 | 7/2001 |
| WO | WO 02/058603 | 8/2002 |
| WO | WO 03/065945 | 8/2003 |
| WO | WO 03/071997 | 9/2003 |
| WO | WO 2006/010556 | 2/2006 |
| WO | WO 2007/030703 | 3/2007 |
| WO | WO 2008/048856 | 4/2008 |
| WO | WO 2008/103789 | 8/2008 |
| WO | WO 2008/141180 | 11/2008 |
| WO | WO 2009/083183 | 7/2009 |
| WO | WO 2009/155537 | 12/2009 |
| WO | WO 2011/007355 | 1/2011 |
| WO | WO 2011/013872 | 2/2011 |
| WO | WO 2011/039517 | 4/2011 |
| WO | WO 2011/057635 | 5/2011 |
| WO | WO 2011/138727 | 11/2011 |
| WO | WO 2011/138728 | 11/2011 |
| WO | WO 2011/138731 | 11/2011 |
| WO | WO 2013/022487 | 2/2013 |
| WO | WO 2013/168165 | 11/2013 |
| WO | WO 2014/081889 | 5/2014 |
| WO | WO 2014/181338 | 11/2014 |
| WO | WO 2014/181339 | 11/2014 |

OTHER PUBLICATIONS

Notice of Allowance Dated Feb. 18, 2014 From the US Patent and Trademark Office Re. U.S. Appl. No. 13/666,513.
Communication Pursuant to Article 94(3) EPC Dated Feb. 11, 2013 From the European Patent Office Re. Application No. 10747082.5.
Official Action Dated Jan. 30, 2013 From the US Patent and Trademark Office Re. U.S. Appl. No. 12/835,838.
Official Action Dated Mar. 5, 2013 From the US Patent and Trademark Office Re. U.S. Appl. No. 13/666,513.
Official Action Dated Mar. 25, 2013 From the US Patent and Trademark Office Re. U.S. Appl. No. 13/666,178.
Official Action Dated May 9, 2013 From the US Patent and Trademark Office Re. U.S. Appl. No. 13/666,461.
Official Action Dated Jul. 1, 2013 From the US Patent and Trademark Office Re. U.S. Appl. No. 13/384,343.
Official Action Dated Jul. 10, 2013 From the US Patent and Trademark Office Re. U.S. Appl. No. 13/680,169.
Official Action Dated Jul. 11, 2013 From the US Patent and Trademark Office Re. U.S. Appl. No. 13/680,161.
Applicant-Initiated Interview Summary Dated Jul. 25, 2013 From the US Patent and Trademark Office Re. U.S. Appl. No. 13/680,161.
Applicant-Initiated Interview Summary Dated Jul. 26, 2013 From the US Patent and Trademark Office Re. U.S. Appl. No. 13/666,513.
Applicant-Initiated Interview Summary Dated Jul. 26, 2013 From the US Patent and Trademark Office Re. U.S. Appl. No. 13/680,169.
Translation of Notification of Office Action Dated Jul. 30, 2013 From the State Intellectual Property Office of the People's Republic of China Re. Application No. 201080032032.X.
Official Action Dated Aug. 29, 2013 From the US Patent and Trademark Office Re. U.S. Appl. No. 12/835,838.
Applicant-Initiated Interview Summary Dated Dec. 13, 2013 From the US Patent and Trademark Office Re. U.S. Appl. No. 13/666,513.
International Search Report and the Written Opinion Dated Dec. 20, 2013 From the International Searching Authority Re. Application No. PCT/IL2013/050401.
Notice of Allowance Dated Nov. 28, 2014 From the US Patent and Trademark Office Re. U.S. Appl. No. 13/384,343.
Notification of Office Action Dated Dec. 2, 2014 From The State Intellectual Property Office of the People's Republic of China Re. Application No. 2011800331827.
Translation Dated Dec. 15, 2014 of Notification of Office Action Dated Dec. 2, 2014 From The State Intellectual Property Office of the People's Republic of China Re. Application No. 2011800331827.
Communication Pursuant to Article 94(3) EPC Dated Dec. 17, 2013 From the European Patent Office Re. Application No. 11723672.9.
Communication Pursuant to Article 94(3) EPC Dated Dec. 19, 2013 From the European Patent Office Re. Application No. 11723674.5.
Communication Pursuant to Article 94(3) EPC Dated Dec. 19, 2013 From the European Patent Office Re. Application No. 11724783.3.
International Search Report and the Written Opinion Dated Dec. 19, 2014 From the International Searching Authority Re. Application No. PCT/IL2014/050416.
International Search Report and the Written Opinion Dated Dec. 19, 2014 From the International Searching Authority Re. Application No. PCT/IL2014/050417.
Official Action Dated Jan. 14, 2014 From the US Patent and Trademark Office Re. U.S. Appl. No. 13/680,161.
Applicant-Initiated Interview Summary Dated Jan. 27, 2014 From the US Patent and Trademark Office Re. U.S. Appl. No. 13/384,343.
Advisory Action Before the Filing of An Appeal Brief Dated Feb. 4, 2014 From the US Patent and Trademark Office Re. U.S. Appl. No. 12/835,838.
Notice of Allowance Dated Mar. 18, 2014 From the US Patent and Trademark Office Re. U.S. Appl. No. 13/666,178.
Advisory Action Before the Filing of An Appeal Brief Dated Mar. 31, 2014 From the US Patent and Trademark Office Re. U.S. Appl. No. 13/384,343.
Notice of Allowance Dated Apr. 4, 2014 From the US Patent and Trademark Office Re. U.S. Appl. No. 13/680,169.
Applicant-Initiated Interview Summary Dated Apr. 14, 2014 From the US Patent and Trademark Office Re. U.S. Appl. No. 13/384,343.
Notice of Allowance Dated Apr. 29, 2014 From the US Patent and Trademark Office Re. U.S. Appl. No. 13/680,161.
Notification of Office Action Dated Apr. 18, 2014 From the State Intellectual Property Office of the People's Republic of China Re. Application No. 201080032032.X and Its Translation Into English.
Search Report Dated Apr. 18, 2014 From the State Intellectual Property Office of the People's Republic of China Re. Application No. 201080032032.X and Its Translation Into English.
Notice of Allowance Dated May 8, 2014 From the US Patent and Trademark Office Re. U.S. Appl. No. 13/666,461.
Notice of Reason for Rejection Dated Apr. 15, 2014 From the Japanese Patent Office Re. Application No. 2012-520149 and Its Translation Into English.
Communication Under Rule 71(3) EPC Dated May 19, 2014 From the European Patent Office Re. Application No. 10747082.5.
Notification of Office Action Dated May 6, 2014 From The State Intellectual Property Office of the People's Republic of China Re. Application No. 2011800331827 and Its Translation Into English.
Search Report Dated May 6, 2014 From The State Intellectual Property Office of the People's Republic of China Re. Application No. 2011800331827 and Its Translation Into English.
Supplemental Notice of Allowability Dated May 21, 2014 From the US Patent and Trademark Office Re. U.S. Appl. No. 13/666,513.
Notice of Allowance Dated Jun. 2, 2014 From the US Patent and Trademark Office Re. U.S. Appl. No. 13/666,178.
Supplemental Notice of Allowability Dated Jun. 23, 2014 From the US Patent and Trademark Office Re. U.S. Appl. No. 13/666,513.
Notification of Office Action Dated May 27, 2014 From The State Intellectual Property Office of the People's Republic of China Re. Application No. 201180033162.X.
Official Action Dated Jun. 26, 2014 From the US Patent and Trademark Office Re. U.S. Appl. No. 13/384,343.
Supplemental Notice of Allowability Dated Jun. 23, 2014 From the US Patent and Trademark Office Re. U.S. Appl. No. 13/680,161.

(56) References Cited

OTHER PUBLICATIONS

Supplemental Notice of Allowability Dated Jun. 27, 2014 From the US Patent and Trademark Office Re. U.S. Appl. No. 13/680,169.
Corrected Notice of Allowability Dated Jul. 8, 2014 From the US Patent and Trademark Office Re. U.S. Appl. No. 13/666,461.
Zhang et al. "Occlusion Effect Comparison of Artificial Silicone Rubber Closure Devices With Different Diameters", Chinese Journal of Tissue Engineering Research, 16(8): 1496-1500, Feb. 19, 2012. Abstract in English.
Official Action Dated Oct. 16, 2013 From the US Patent and Trademark Office Re. U.S. Appl. No. 13/666,513.
Official Action Dated Oct. 18, 2013 From the US Patent and Trademark Office Re. U.S. Appl. No. 13/384,343.
Official Action Dated Nov. 7, 2013 From the US Patent and Trademark Office Re. U.S. Appl. No. 13/666,178.
Official Action Dated Nov. 7, 2013 From the US Patent and Trademark Office Re. U.S. Appl. No. 13/680,169.
Official Action Dated Nov. 13, 2013 From the US Patent and Trademark Office Re. U.S. Appl. No. 13/666,461.
Communication Pursuant to Article 94(3) EPC Dated Nov. 5, 2014 From the European Patent Office Re. Application No. 11724783.3.
Communication Relating to the Results of the Partial International Search Dated Sep. 16, 2014 From the International Searching Authority Re. Application No. PCT/IL2014/050416.
Communication Relating to the Results of the Partial International Search Dated Sep. 16, 2014 From the International Searching Authority Re. Application No. PCT/IL2014/050417.
International Preliminary Report on Patentability Dated Nov. 20, 2014 From the International Bureau of WIPO Re. Application No. PCT/IL2013/050401.
Notice of Allowance Dated Oct. 1, 2014 From the US Patent and Trademark Office Re. U.S. Appl. No. 12/835,838.
Notification of Office Action and Search Report Dated Oct. 20, 2014 From the State Intellectual Property Office of the People's Republic of China Re. Application No. 201080032032.X and Its Translation Into English.
Summons to Attend Oral Proceedings Pursuant to Rule 115(1) EPC Dated Nov. 22, 2013 From the European Patent Office Re. Application No. 10747082.5.
International Preliminary Report on Patentability Dated Nov. 15, 2012 From the International Bureau of WIPO Re. Application No. PCT/IB2011/051936.
Communication Relating to the Results of the Partial International Search Dated Aug. 12, 2011 From the International Searching Authority Re. Application No. PCT/IB2011/051932.
Communication Relating to the Results of the Partial International Search Dated Aug. 16, 2011 From the International Searching Authority Re. Application No. PCT/IB2011/051933.
Communication Relating to the Results of the Partial International Search Dated Nov. 17, 2010 From the International Searching Authority Re. Application No. PCT/IL2010/000565.
Communication Relating to the Results of the Partial International Search Dated Aug. 18, 2011 From the International Searching Authority Re: Application No. PCT/IB2011/051938.
International Preliminary Report on Patentability Dated Jun. 1, 2012 From the International Preliminary Examining Authority Re. Application No. PCT/IB2011/051933.
International Preliminary Report on Patentability Dated Jun. 5, 2012 From the International Preliminary Examining Authority Re. Application No. PCT/IB2011/051932.
International Preliminary Report on Patentability Dated Sep. 6, 2012 From the International Preliminary Examining Authority Re. Application No. PCT/IB2011/051938.
International Preliminary Report on Patentability Dated Oct. 31, 2011 From the International Preliminary Examining Authority Re. Application No. PCT/IL2010/000565.
International Search Report and the Written Opinion Dated Oct. 14, 2011 From the International Searching Authority Re. Application No. PCT/IB2011/051933.
International Search Report and the Written Opinion Dated Oct. 17, 2011 From the International Searching Authority Re. Application No. PCT/IB2011/051932.
International Search Report and the Written Opinion Dated Aug. 18, 2011 From the International Searching Authority Re. Application No. PCT/IB2011/051936.
International Search Report and the Written Opinion Dated Oct. 19, 2011 From the International Searching Authority Re: Application No. PCT/IB2011/051938.
International Search Report and the Written Opinion Dated Feb. 28, 2011 From the International Searching Authority Re. Application No. PCT/IL2010/000565.
Invitation to Pay Additional Fees Dated Oct. 7, 2011 From the International Preliminary Examining Authority Re. Application No. PCT/IL2010/000565.
Notification Concerning Informal Communications With the Applicant Dated May 3, 2012 From the International Searching Authority Re: Application No. PCT/IB2011/051938.
Notification Concerning Informal Communications With the Applicant Dated May 4, 2012 From the International Searching Authority Re: Application No. PCT/IB2011/051933.
Notification Concerning Informal Communications With the Applicant Dated May 18, 2012 From the International Searching Authority Re: Application No. PCT/IB2011/051932.
Response Dated May 30, 2011 to the Written Opinion of Feb. 28, 2011 From the International Searching Authority Re. Application No. PCT/IL2010/000565.
Restriction Official Action Dated Oct. 15, 2012 From the US Patent and Trademark Office Re. U.S. Appl. No. 12/835,838.
Written Opinion Dated Jun. 1, 2012 From the International Preliminary Examining Authority Re. Application No. PCT/IB2011/051938.

* cited by examiner

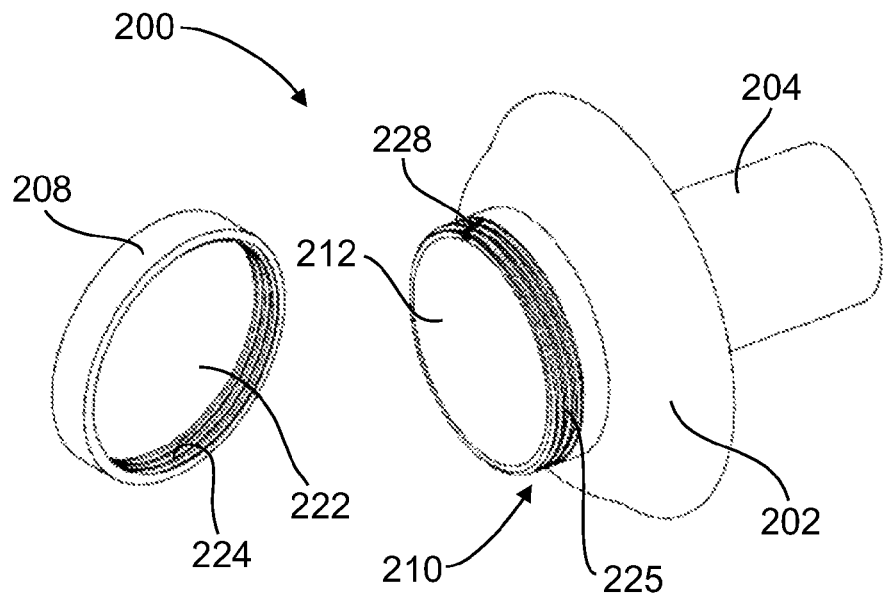
Figure 5
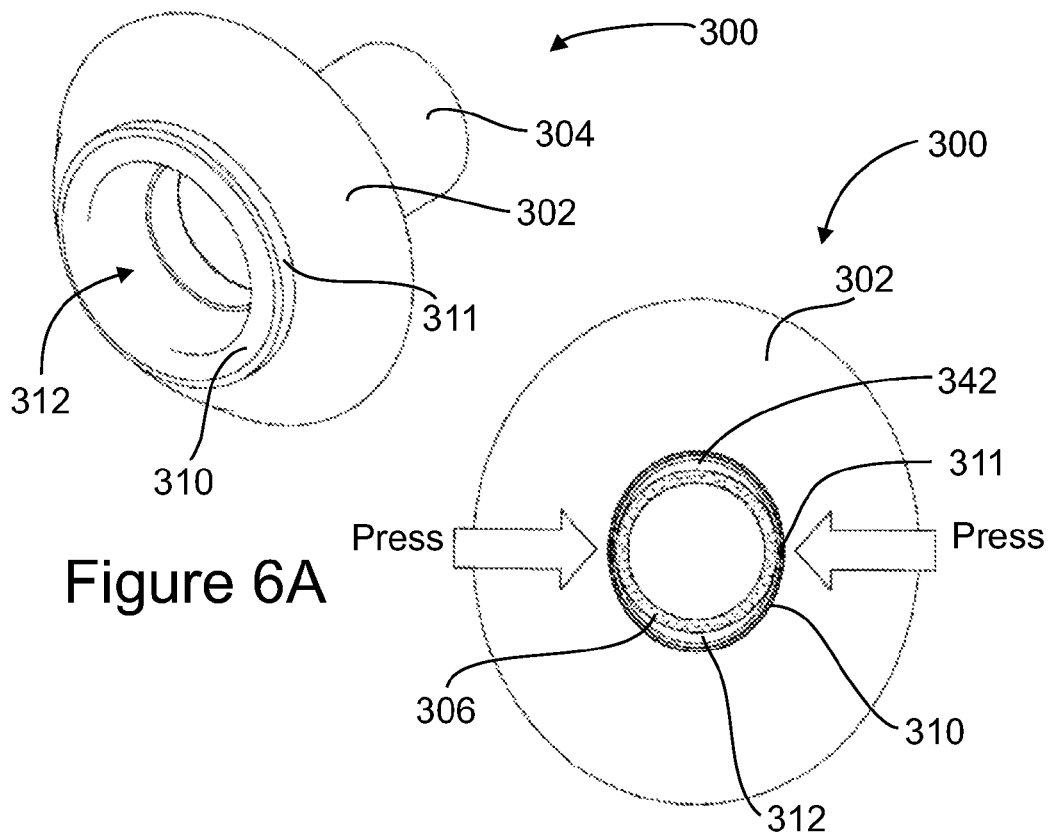
Figure 6A
Figure 6B

OSTOMY PORT GAS RELEASE MECHANISM

RELATED APPLICATIONS

This application is a Continuation of PCT Patent Application No. PCT/IB2011/051932 having International filing date of May 2, 2011, which claims the benefit of priority under 35 USC 119(e) of U.S. Provisional Patent Application No. 61/330,359 filed on May 2, 2010 and U.S. Provisional Patent Application No. 61/431,084 filed on 10 Jan. 2011. PCT Patent Application No. PCT/IB2011/051932 is also a Continuation-In-Part (CIP) of PCT/IL2010/000565 filed Jul. 14, 2010, which claims the benefit of priority under 35 USC 119(e) of U.S. Provisional Patent Application No. 61/225,546 filed on Jul. 14, 2009 and U.S. Provisional Patent Application No. 61/330,359 filed on May 2, 2010. The contents of the above applications are all incorporated herein by reference as if fully set forth in their entirety.

PCT Patent Application No. PCT/IB2011/051932 is also related to PCT Patent Application Nos. PCT/IB2011/051933, PCT/IB2011/051938 and PCT/IB2011/051936, which were all filed by, inter alia, Applicant Stimatix GI Ltd., concurrently with PCT Patent Application No. PCT/IB2011/051932, the disclosures of which are incorporated herein by reference.

FIELD AND BACKGROUND OF THE INVENTION

The present invention, in some embodiments thereof, relates to ostomy ports and, more particularly, but not exclusively, to a gas release mechanism for an ostomy port.

Controlling gas (flatulation) releasing in an ostomy port is generally desirable for preventing possible risk and/or discomfort to a user of the port resulting from accumulation of intestinal flatus. Embarrassment and/or discomfort may additionally result from unintended releasing of flatus in an undesirable manner to the port's user. Some methods used in the art attempt to solve the problem by including mechanisms in colostomy bags which are attached to the ostomy port, while others include gas release mechanisms in the ports.

U.S. Patent Application Publication No. 2008/0275410 relates to "a colostomy bag with a vent and a method for venting gas collected in the colostomy bag. A dual vent and cap assembly attached to a colostomy bag vents gas trapped in the bag either continuously or as periodically desired by a user. A method for venting gas collected in the colostomy bag provides that replacement and/or cleaning of the colostomy bag is reduced. Also, a method of using a disposable sleeve in combination with a clip may be used to hygienically clean the colostomy bag."

U.S. Pat. No. 6,033,390 relates to "a continent ostomy port device has a face plate defining an aperture alignable with the opening of a stoma in the user's body and a closure adjacent to the aperture is adapted to permit covering and uncovering of the aperture in the face plate. A catheter extends from one side of the face plate proximally, and one end of the catheter is disposed within the ostomy site when the port device is in use. The catheter has continuous exterior and interior side walls, the latter defining a major lumen and is sized and shaped for non-surgical insertion through a stoma to a sufficient distance that the presence of the catheter within the stoma provides a barrier which reduces the incidence of prolapse, without the use of extraneous, externally applied materials or additional surgery. A removable cartridge fits snugly and slideably within the major lumen of the catheter of the device so as to prevent inadvertent escape of body waste material from the stoma when the cartridge is in place, without use of an ostomy bag, and to clean the interior side wall of the catheter as the cartridge is pressed into the major lumen. An anti-reflux valve is activated to prevent escape of body waste and deactivated for passage of fluid. Retaining structure is connected to the catheter, and is non-surgically, snugly fittable into the stoma, to cause the port device to be self-retaining in a normal use position within a stoma, without surgery or fixation materials."

U.S. Pat. No. 5,125,916 to Panebianco et al., describes "An ostomy appliance is disclosed for selectively sealing a stoma. The appliance includes a central elongated relatively rigid tube having inner and outer end portions. A cap is support to the outer end portion of the tube and is adapted to engage the users' skin when the tube is inserted in a stoma. A flexible extendable and collapsible bellows is mounted on the inner end of the tube for sealing the inside of the stoma when the appliance is inserted therein. A flexible rod insertable through the cap and tube for engagement with the bellows extends the bellows to collapse it for insertion in the stoma.

Additional background art includes U.S. Pat. No. 5,658,267; U.S. Pat. No. 4,810,250; US Patent Application Publication No. 2006/0106354 A1; U.S. Pat. No. 4,030,500; U.S. Pat. No. 4,121,589; U.S. Pat. No. 5,045,052; U.S. Pat. No. 6,485,476 B1; US Patent Application Publication No. 2008/0275410 A; U.S. Pat. No. 4,211,224; U.S. Pat. No. 4,338,937; U.S. Pat. No. 4,662,890; U.S. Pat. No. 5,569,216; US Patent Application Publication No. 2010/0174253; and U.S. Pat. No. 4,516,974.

SUMMARY OF THE INVENTION

There is provided in accordance with an exemplary embodiment of the invention a method of controlled gas release from an ostomy port, comprising:

(a) determining that there is a need to release gas from a body of a patient;

(b) temporarily opening a pathway from said body to an outside thereof.

Optionally, said determining comprises determining by an automatic mechanism. Optionally or alternatively, said determining comprises determining by a human. Optionally or alternatively, said determining comprises determining in response to a sensor.

In an exemplary embodiment of the invention, said opening comprises opening a valve in a dedicated exhaust lumen.

In an exemplary embodiment of the invention, said opening comprises opening a gap between said port and a seal thereof.

In an exemplary embodiment of the invention, said pathway includes a stench negating material therein.

In an exemplary embodiment of the invention, said pathway includes a filter therein.

In an exemplary embodiment of the invention, the method comprises repeating said determining and said releasing at least two times in 24 hours, for at least 5 days in a period of 30 days and not while irrigating through said passageway.

There is provided in accordance with an exemplary embodiment of the invention an ostomy port, comprising:

(a) a blocked channel for waste conduction from inside the body to out of the body;

(b) a selectively open gas pathway communicating with one or both of said channel and said inside of the body and which at least partially does not overlap with said waste conduction channel. Optionally, said blocked channel is manually openable. Optionally or alternatively, said gas pathway includes a gap between said channel and a body of said port. Optionally, the port comprises at least one distortable component which, when distorted, provides said gap.

In an exemplary embodiment of the invention, the port comprises at least one movable element which, when moved, provides said gap. Optionally, said motion comprises motion in a plane perpendicular to an axis of said channel In an exemplary embodiment of the invention, said gas pathway includes at least one dedicated lumen.

In an exemplary embodiment of the invention, said gas pathway includes a plurality of lumens.

In an exemplary embodiment of the invention, said gas pathway includes a plurality of openings into said channel.

In an exemplary embodiment of the invention, said gas pathway includes a stench treating material.

In an exemplary embodiment of the invention, said gas pathway includes a valve. Optionally, said gas pathway includes an automatically actuated valve.

In an exemplary embodiment of the invention, said gas pathway includes a pressure sensor which generates a signal in response to a pressure level.

There is provided in accordance with an exemplary embodiment of the invention an ostomy port, comprising:
(a) a blocked channel for waste conduction from inside the body to out of the body;
(b) an open gas pathway integral to said port communicating with one or both of said channel and said inside of the body and which at least partially does not overlap with said waste conduction channel. Optionally, said gas pathway is a filtering pathway.

There is provided in accordance with an exemplary embodiment of the invention an ostomy port, comprising:
(a) a channel for waste conduction from inside the body to out of the body;
(b) a waste collection bag at a terminus of said channel; and
(c) a gas release pathway configured for releasing gas from inside of said body or said port and which does not pass through said bag.

There is provided in accordance with an exemplary embodiment of the invention an ostomy component, comprising:
(a) a cap suitable for an ostomoy port; and
(b) a coupling device configured to couple said cap to said port and to provide selective gas release.

In an exemplary embodiment of the invention, said coupling device is adapted to rotate relative to said port and provide a gap for gas release from said port. Optionally or alternatively, said coupling device is adapted to be distorted manually and provide a gap for gas release from said port.

There is provided in accordance with an exemplary embodiment of the invention an ostomy component, comprising:
(a) a cap suitable for an ostomy port; and
(b) a coupling device configured to couple said cap to said port and to provide filtered gas release. Optionally, the component comprises
a waste collection bag attached or integral to said cap.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 5 schematically illustrates an exemplary gas release mechanism including a threaded cover for attachment to a stomal cover in an ostomy port, according to some embodiments of the present invention;

FIGS. 6A and 6B show schematically illustrates an exemplary gas release mechanism including a cap and a deformable fixation element for attachment to a stomal cover in an ostomy port, according to some embodiments of the present invention;

DESCRIPTION OF SPECIFIC EMBODIMENTS OF THE INVENTION

Figure 1:
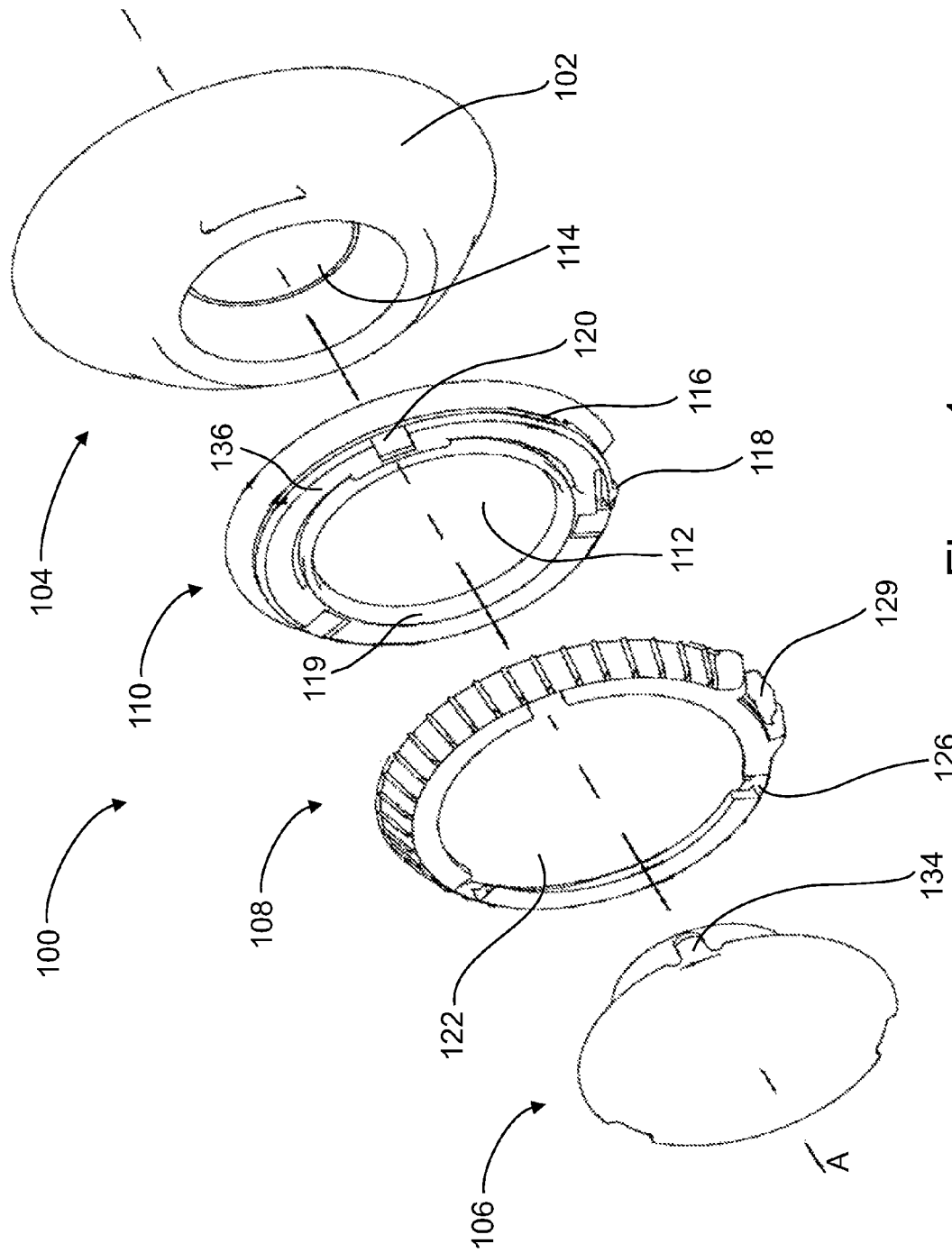
FIG. 1 schematically illustrates an exploded perspective view of an exemplary gas release mechanism including a rotary cover for attachment to a stomal cover of an ostomy port for providing a gas flow path from an interior of the ostomy port to the ambient, according to an embodiment of the present invention.

The present invention, in some embodiments thereof, relates to ostomy ports and, more particularly, but not exclusively, to a gas release mechanism for an ostomy port. The gas release mechanism, in some embodiments, is controlled by a user for actively releasing gas from the interior of the ostomy port to the ambient. In other embodiments, the mechanism includes ventilation means for passively (not user controlled) releasing the gases to the ambient. Actively or passively releasing the gases in the ostomy port may prevent embarrassing situations to the user wherein large discharges of gases are made at one time and/or may prevent discomfort to the user due to gas pressure buildup.

Reference hereinafter to an ostomy port or a stomal cover may include, for example, any of the embodiments described in any one of the applications from which this disclosure is claiming benefit and referenced in the above section Related Application.

As used hereinafter, the term "distal" refers to away from the proximal opening and towards an interior of the abdominal cavity while "proximal" refers to away from the abdominal cavity towards the proximal opening of the ostomy port (and away from the body).

As used hereinafter, "ostomy port" is any device that is intended to be inserted into a stoma and to be worn on a user's body, and includes a conduit through which waste matter can pass from an intestinal portion inside an abdominal cavity to an outside of the body. The ostomy port may include a stomal cover worn externally on the abdominal wall.

An aspect of some embodiments of the present invention relates to a gas release mechanism having a fixation element attached to a stomal cover of an ostomy port, and a cover movably coupled to the fixation element. The fixation element and the cover are in fluid communication with a proximal opening of the ostomy port for providing a gas flow path from an interior of the ostomy port to the ambient.

In some exemplary embodiments, a cover is rotationally coupled to the fixation element so that rotation of the cover about its axis in a first direction, for example clockwise, opens the gas flow path while rotation in an opposite second direction (e.g. counterclockwise) closes the gas flow path. Additionally or alternatively, rotation in the first direction open the gas flow path while further rotation in the same direction closes the gas flow path.

A particular advantage of some embodiments of the invention is that when manipulating the port, no force is applied towards the body or away from the body. Rather, force is applied in a plane parallel to the body surface and perpendicular to the axis of the ostomy port, for example, translation or rotation forces.

In some exemplary embodiments, the cover is pivotally coupled to the fixation element for opening a gas flow path on an upper section (in the direction of the head of the user) of the proximal opening while maintaining a lower section of the opening sealed to prevent waste content leakage. Optionally, pivoting the cover in a proximal direction relative to the fixation element opens the gas flow path. Returning the pivoted cover to its original position seals the gas flow path. Additionally or alternatively, pivoting the cover laterally relative to the fixation element (in the same plane as the element) opens the gas flow path.

In some exemplary embodiments, the fixation element is annularly shaped and attached to the stomal cover surrounding the proximal opening of the ostomy port. Alternatively, the fixation element is adapted to allow pivoting of the cover relative to the proximal opening. In some embodiments, the fixation element is attachable to ostomy ports known in the art for attaching the gas release mechanisms described herein to the ports when the ports are manufactured. Additionally or alternatively, the gas release mechanisms described herein are retrofitted onto existing ports.

In some exemplary embodiments, the fixation element includes a rigid material such as, for example, a polymer or other plastic material. Alternatively, the fixation element includes a non-plastic material resistant to contact with waste content discharged through the proximal opening. Optionally, the fixation element is attached to the stomal cover using techniques known in the art such as, for example, over-molding, bonding, welding, or any combination thereof.

In some exemplary embodiments, a fastening mechanism between the cover and the fixation ring allows for clockwise and counter-clockwise rotation of the cover while preventing axial displacement of the cover relative to the fixation element. Alternatively, the fastening mechanism includes axial displacement of the cover relative to the fixation element, for example, as when mechanical threads are used. The threading may be set such that for complete locking, the cover may be rotated by any number of revolutions, from a fraction of a revolution (e.g. ¼ or ⅛ of a revolution) up to a few revolutions (typically less than 3). Optionally, a depth of the threads may be set between 0.5 mm and 2 or 3 mm such that attachment between the cover and the stomal cover withstands a pulling force of between 0.5 and 5 kg, for example 2 kg.

Optionally, the fastening mechanism allows for an increase in contact pressure between the cover and the fixation element when the cover is rotated in the clockwise direction and for a decrease in contact pressure when rotation is in the counter-clockwise direction.

In some exemplary embodiments, the cover is annularly shaped having an opening for sealingly accommodating a cap against the stomal cover. Optionally, rotation of the cover in the clockwise direction presses the cap against the fixation element and/or against the ostomy port and seals the proximal opening so that the gas flow path is closed. Additionally, rotation of the cover in the counter-clockwise direction displaces the cap away from the fixation element and from the proximal opening so that the gas flow path is opened. Optionally, cap displacement from sealed position is gradually increased (decreased) as the cover is rotated in the counter-clockwise (clockwise) direction, allowing the user to create a flow path in which only gas can flow but liquid or solid matter is retained in the ostomy port. The gas flow path size, and thereby the amount of displacement of the cap, is set by the user rotating the cover, and may be on the order of tens of microns and optionally not exceeding 500 microns, for example, 50 microns, 70 microns, 100 microns, 150 microns, 200 microns. Optionally, the displacement is greater in an upper section of the cap relative to a lower section of the cap for allowing the gas flow path to be through the upper section and for maintaining a better seal in the lower section for preventing leakage of waste content.

In some exemplary embodiments, the gas release rate is set by the user by the degree to which the rotary slider is rotated.

The release rate may vary according to the degree of stool liquidity and on separation between gaseous waste and liquid or solid waste behind the proximal opening of the ostomy port. Optionally, for relatively loose and/or mixed content (where gaseous and liquid/solid waste is mixed distally to the proximal opening), a low release rate may be used, for example on the order of 1 ml/sec, in order to avoid leakage of fecal waste. Additionally, for relatively firm and/or separated content (where mainly gaseous waste is present distally to the proximal opening), higher release rate may be used, for example up to order of 30-50 ml/sec.

In some exemplary embodiments, a locking mechanism secures the cover to the fixation element when the gas flow path is closed, requiring the user to apply a force overcoming the locking mechanism for opening the gas flow path. Optionally, the cover includes a safety catch to prevent undesired removal of the cap from the cover. Optionally, the cap includes a removable cap cover and a deployable waste collection bag for collecting the waste in the ostomy port. Alternatively, the waste collection bag is separately attached to the cap following cap cover removal, or not at all.

An aspect of some embodiments of the present invention relates to a gas release mechanism having a fixation element with an elastically deformable opening which surrounds the proximal opening on the stomal cover. The fixation element sealingly accommodates a cap in the opening when in a pre-deformed state. Optionally, the cap may be similar to that previously described. The deformable opening allows for a gas flow path between an interior of the ostomy port and the ambient when a user presses on a rim of the fixation element for elastically deforming the opening. The fixation ring may be deformable by a pressing force ranging, for example, from 100-1000 grams, for example 200 grams, 350 grams, 500 grams, 650 grams, for enabling convenient activation of the gas release mechanism while preventing deformation due to inadvertent forces. The gas flow path size is set by the user pressing on the fixation element, and may be on the order of tens of microns and not exceeding 200 microns, for example, 50 microns, 70 microns, 100 microns, 130 microns, 150 microns. Optionally, the user presses laterally on opposite sides of the rim for deforming the opening. Additionally or alternatively, a clamp may be fitted around the rim which deforms the opening when pressed by the user. Optionally, a bottom section of the opening (in a direction towards the user's legs) is non-deformable so that the user presses on an upper section of the opening for causing the deformation and opening the gas flow path.

In some exemplary embodiments, the fixation element is annularly shaped. Alternatively, the fixation element may be non-circular and may include a circular opening. Optionally, the fixation element may include an elastomer. Additionally or alternatively, the fixation element includes a rigid material, for example, a polymer or other plastic material. Optionally, the fixation element is attached to the stomal cover using techniques known in the art such as, for example, over-molding, bonding, welding, or any combination thereof. Alternatively, the fixation element is an integral part of the stomal cover.

Another aspect of some embodiments of the present invention relates to a gas release mechanism having a ventilation port in the stomal cover in fluid communication with an interior of the ostomy port through at least one lumen. Optionally, the at least one lumen includes an opening at a distal end inside the ostomy port through which gas enters the lumen and flows to the ventilation port (and thereon released into the ambient). Additionally or alternatively, the at least one lumen includes a plurality of openings for gas flow through the lumen to the ventilation port.

A lumen diameter may be in the range of 0.5-3 mm, for example, 1.5 mm, 2 mm, 2.5 mm. A lumen length may extend along the entire length of the ostomy port. Alternatively, the lumen may extend along a portion of the length of the ostomy port. A size of the openings may be on the order of tens of microns and not exceeding 500 microns, for example, 50 microns, 70 microns, 100 microns, 150 microns, 200 microns. The at least one lumen may include a plurality of lumens. Optionally, the at least one lumen is positioned on an upper section of the ostomy port to substantially prevent waste content from entering through the opening or openings. Additionally or alternatively, the openings are of a size which allows gas flow through the openings into the at least one lumen and substantially prevents waste content flow through the opening. In some embodiments, the ventilation port and the at least one lumen can be used for irrigation purposes, an irrigation fluid applied through the ventilation port into the lumen. Additionally or alternatively, the lumen includes open-celled foam for supporting the walls of the lumen while allowing gas flow through the lumen.

In some exemplary embodiments, the ventilation port includes a valve for allowing a user to control the release of gas flow from the interior of the ostomy port. Optionally, the valve includes a stopcock. Alternatively, the valve includes a Schrader valve or other valve suitable for fitting into the ventilation port and for controlling the release of gas. A pressing force by the user, ranging from 100-1000 grams, for example 200 grams, 350 grams, 500 grams, 650 grams, may be used to activate the valve for preventing inadvertent operation. Additionally or alternatively, the valve may be automatically activated by a pressure sensing mechanism sensing an increase in pressure in the ostomy port. For relatively loose and/or mixed content (where gaseous and liquid/solid waste is mixed behind the proximal opening), a low release rate may be used, for example on the order of 1 ml/sec, in order to avoid leakage of fecal waste. For relatively firm and/or separated content (where mainly gaseous waste is present behind the proximal opening), higher release rate may be used, for example up to order of 30-50 ml/sec.

In some exemplary embodiments, the ventilation port includes a housing for accommodating a filter for filtering the gas flowing from the interior of the ostomy port. The filter is replaceable and is optionally replaced each time the collection bag is replaced (or emptied in the case of reusable bags), for example, about 1-3 times a day. Filter replacement may require a higher frequency in case of loose and/or mixed content (e.g. in ileostomy) where the filter might be blocked. Optionally, the filter is a charcoal filter or any filter suitable for deodorizing the passing gas so that it will not be perceived by other persons in proximity to the user.

An aspect of some embodiments of the present invention relates to a cap insertable into the proximal opening of the ostomy port and having a gas filter through which gas may flow to the ambient. Optionally, the cap includes a waste collection bag. The filter is located on the cap such that it is exposed to the ambient at all times while the cap in inserted in the proximal opening. Optionally, the filter is exposed to the ambient for providing a gas flow path when the waste content bag is deployed. Alternatively, the filter is on the waste collection bag.

In some exemplary embodiments, a pressure sensor (not shown) is assembled in an interior of the ostomy port, for example on an internal wall of the ostomy port, and a control unit is assembled at a portion of the ostomy port externally to the user's body, for example on the stomal cover. The control unit receives pressure signals from said pressure sensor, and is programmed with a logic algorithm for selectively opening a gas release valve upon fulfillment of predetermined conditions, for example any of the following conditions:

a. Internal pressure is greater than 60 mmHg for more than 1 min;
   b. Internal pressure is greater than 100 mmHg for more than 10 sec;
   c. Internal pressure is greater than 150 mmHg, immediate release.

Optionally, the ostomy port is equipped with an indication mechanism, for example visual, audible or vibrational alarm, or a transmitter or wireless signals (e.g., bluetooth) to notify the user of an activation of the gas release valve.

Additionally or alternatively, the control unit notifies the user on a need to release gas without automatically activating the gas release valve, or with a delay, such as, for example, 1-5 minutes. Optionally, the gas release valve can be closed either manually by the user or automatically by said control unit when the internal pressure decreases, for example, to no greater than 30 mmHg.

In some exemplary embodiments, a pressure sensor and a control unit as those described above control the opening of a gas release valve and/or deploying of a disposable collection bag, according to a predetermined logic, for example:

a. As (e.g., if/when) internal pressure is greater than 60 mmHg for more than 1 min, open the gas release valve;
   b. As internal pressure is greater than 60 mmHg for more than 2 min, deploy the disposable collection bag;
   c. As internal pressure is greater than 100 mmHg for more than 10 sec, open the gas release valve;
   d. As internal pressure is greater than 100 mmHg for more than 30 sec, deploy the disposable collection bag;
   e. As internal pressure is greater than 150 mmHg, open the gas release valve immediately;
   f. As internal pressure is greater than 150 mmHg, deploy the disposable collection bag immediately;

Optionally, the pressure sensor includes a mechanical or electro-mechanical control. Additionally or alternative, the pressure sensor may include an override mechanism for allowing the user to decide to open the gas release valve when alerted that the internal pressure has exceeded the predetermined levels. Optionally, the gas release valve can be closed either manually by the user or automatically by a controller when the internal pressure decreases, for example, to no greater than 30 mmHg if the ostomy bag has not been deployed.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Reference is made to FIG. 1 which schematically illustrates an exploded perspective view of an exemplary gas release mechanism 100 for attachment to a stomal cover 102 of an ostomy port 104 for providing a gas flow path from an interior of the ostomy port to the ambient, according to an embodiment of the present invention. Optionally, gas release mechanism 100 includes a cap 106, a cover 108, and a fixation element such as, for example, fixation ring 110.

Figure 2:
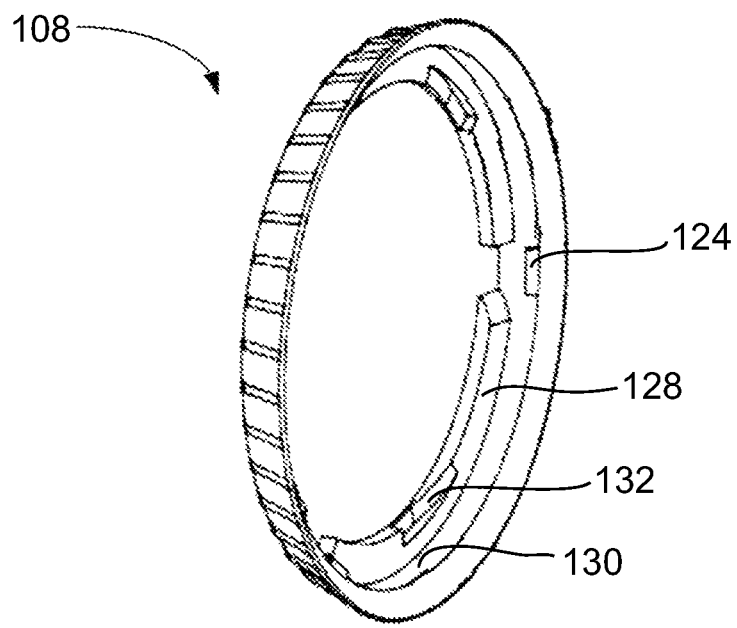
FIG. 2 schematically illustrates a perspective view of an underside of the rotary cover shown in FIG. 1, according to an embodiment of the present invention.
Figure 3:
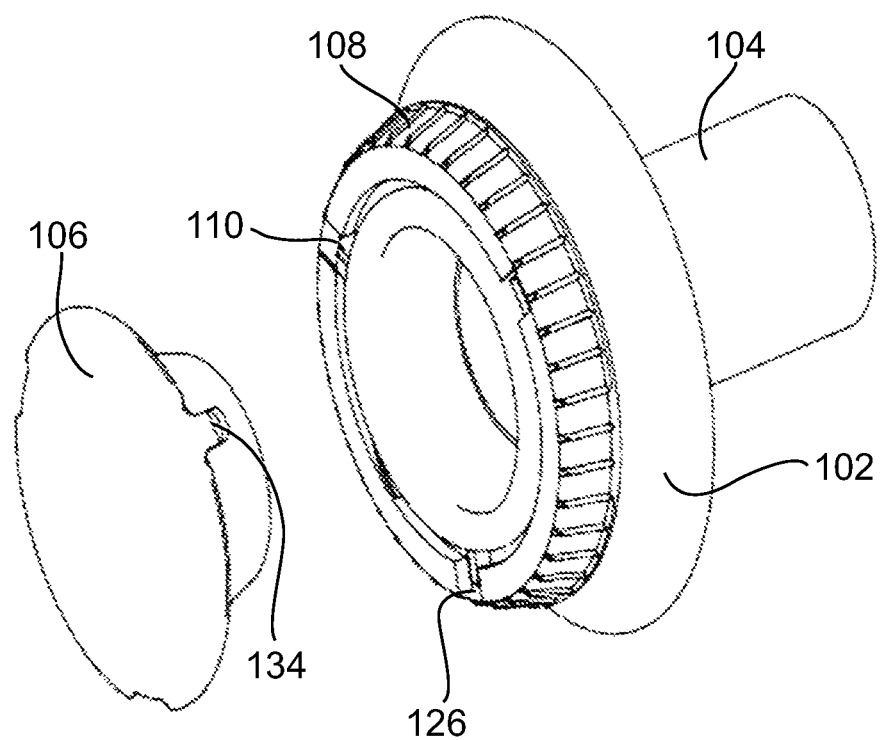
FIG. 3 schematically illustrates the ostomy port with the rotary cover and the fixation ring attached to stomal insert, according to an embodiment of the present invention.

Reference is now also made to FIG. 2 which schematically illustrates a perspective view of an underside of cover 108, and to FIG. 3 which schematically illustrates ostomy port 104 with cover 108 and fixation ring 110 attached to stomal cover 102, according to an embodiment of the present invention.

In some exemplary embodiments, fixation ring 110 is annular shaped and includes an opening 112. Fixation ring 110 is attached to stomal cover 102 with opening 112 fitting over a proximal opening 114 on the stomal cover, their centers substantially aligned along a central axis A. A recess 116 extends along the whole circumference of fixation element 110. Alternatively, recess 116 extends along a portion of the circumference of fixation ring 110. Recess 116 is part of a fastening mechanism which allows clockwise and counter-clockwise rotation of cover 108 relative to fixation element 110 and prevents unwanted axial displacement of the cover relative to the fixation element.

A locking mechanism 118 is included for locking cover 108 in position when the gas flow path is closed. Locking mechanism 118 includes a lever which interacts with a recess on cover 108 for providing a warning to a user, for example by a "clicking" noise (sensation) when the cover is locked. Alternatively, locking mechanism 118 locks cover 108 in position when the gas flow path is open.

Further included is a circumferential wall 119 for sealingly securing cap 106 against fixation element 110 when the gas flow path is closed. A plurality of slots 120, for example three slots, are included in circumferential wall 119 for substantially restricting rotational movement of securing cap 106 relative to fixation element 110 when the gas flow path is closed.

In some exemplary embodiment, cover 108 is annular shaped and includes an opening 122. Cover 108 is rotably attachable to fixation element 110 with a center of opening 122 substantially aligned with fixation ring 110 along axis A for properly attaching the cover onto the fixation ring.

Included in cover 108 is a plurality of tabs 124, for example three tabs, forming part of the fastening mechanism coupling cover 108 and fixing element 110. Tabs 124 fit into recess 116 in fixation ring 110 and slide along the recess, allowing cover 108 to rotate clockwise and counterclockwise. Additionally, tabs 124 are sized to fit into recess 116 for substantially preventing cover 108 displacement in an axial direction.

Further included in cover 108 is a plurality of slots 126, for example three slots, and a rim 128 extending between the slots along an inside wall 130 of the cover, configured for enabling cap 106 to be inserted into opening 122 and secured to fixation ring 110. Optionally, rim 128 includes a varying thickness along its whole length for pushing cap 106 in a direction away from proximal opening 114 as cover 108 is rotated for opening the gas flow path. Additionally or alternatively, the varying thickness in rim 128 is for pushing cap 106 towards proximal opening 114 as cover is 108 is rotated for closing the gas flow path. Alternatively, the varying thickness is along a portion of the length of rim 128. Alternatively, rim 128 includes one or more inclined surfaces 132 for pushing cap 106 in a direction towards proximal opening 114. Additionally or alternatively, inclined surfaces 132 push cap 106 away from proximal opening. Optionally, rim 128 and/or inclined surfaces 132 may be dimensioned for pushing on cap 106 so that an upper section of the cap is further pushed away from proximal opening 114 relative to a lower section.

Included in cover 108 is safety catch 129 for preventing inadvertent removal of cap 106 from the cover. Safety catch 129 is depressed for allowing cover 108 to be brought to a position where cap 106 may be removed from the cover.

In some exemplary embodiments, cap 106 is adapted to be axially displaced by cover 108 towards proximal opening 114 for closing the gas flow path, or away from the opening for opening the gas flow path, depending on the direction of rotation of the cover. Cap 106 includes a plurality of tabs 134 insertable through slots 126 in cover 108 into slots 120 in fixation ring 110 for sealing proximal opening 114. Cap 106 may be locked against proximal opening 114 by rotating cover 108 so that tabs 134 are no longer aligned with slots 126 in the cover but are now pressed between rim 128 and slots 120.

Figure 4B:
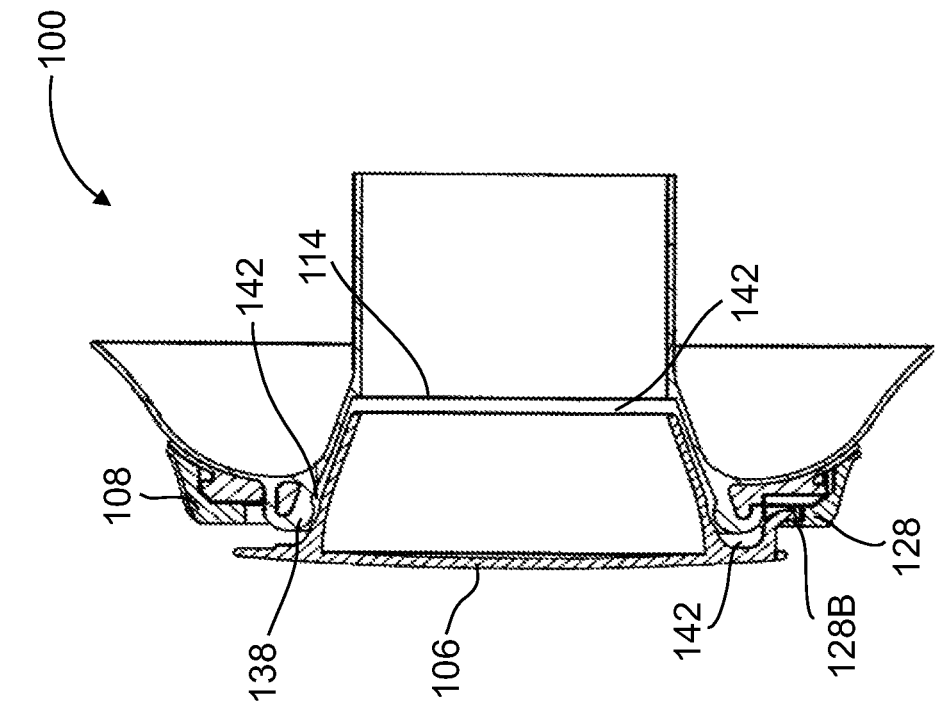
FIG. 4B schematically illustrates a sectional view of the gas release mechanism including the rotary cover in the ostomy port in an open gas flow path configuration, according to some embodiments of the present invention.
Figure 4A:
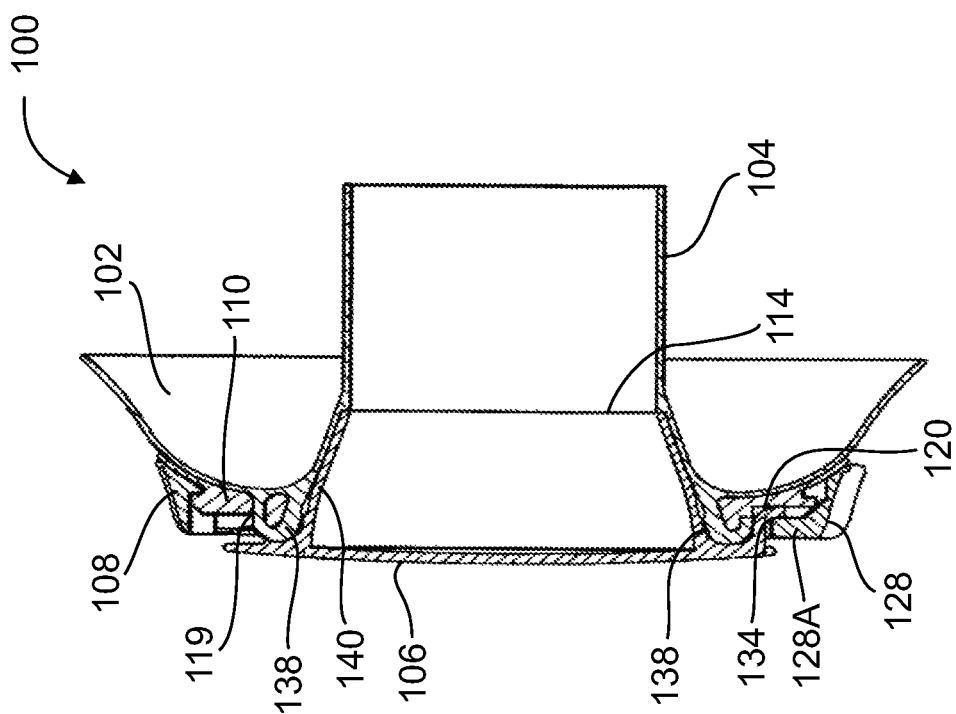
FIG. 4A schematically illustrates a sectional view of the gas release mechanism including the rotary cover in the ostomy port in a closed gas flow path configuration, according to some embodiments of the present invention.
Figure 4C:
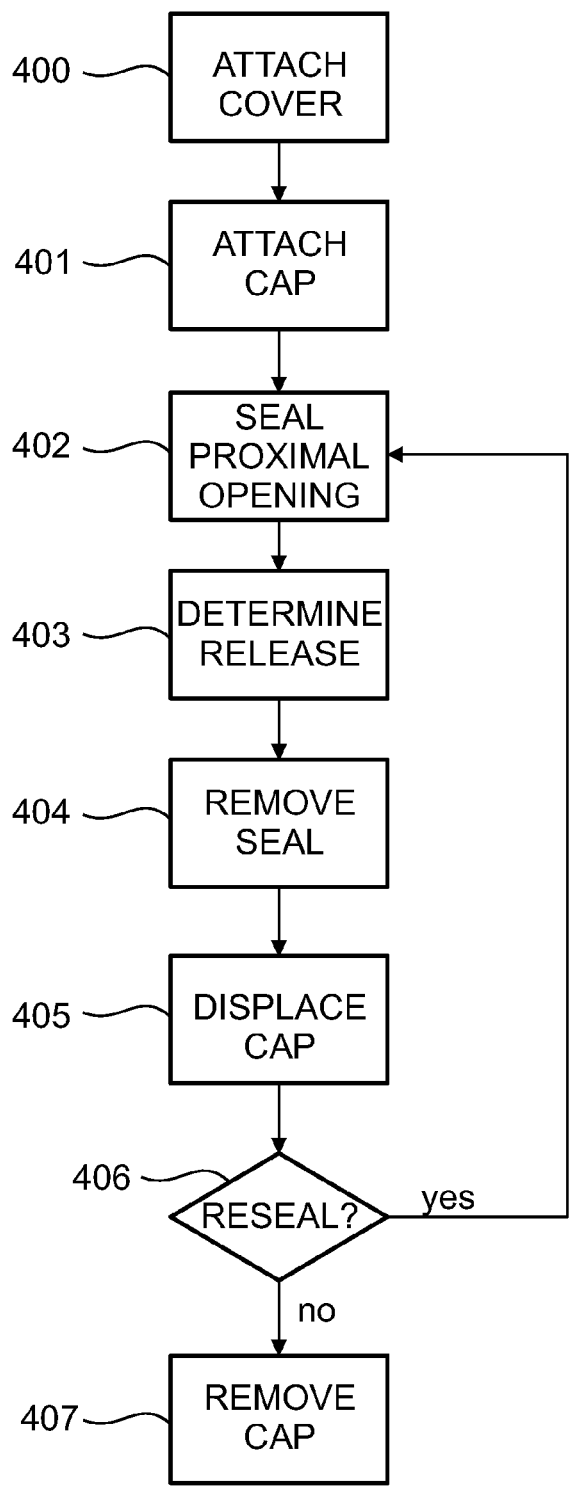
FIG. 4C illustrates a flow chart of a method of releasing gas using the gas release mechanism including the rotary cover, according to some exemplary embodiments of the present invention.

Reference is now also made to FIGS. 4A and 4B which schematically illustrate sectional views of gas release mechanism 100 in ostomy port 104, in a closed gas flow path configuration and an open gas flow path configuration, respectively, according to some embodiments of the present invention. In FIG. 4A, cap 106 seals proximal opening 114 for preventing waste contents and gas from escaping from ostomy port 104. In FIG. 4B, cap 106 is displaced away from proximal opening 114 for releasing gas from ostomy port 104 while preventing waste content from leaking out from the ostomy port. To achieve these configurations, reference is now also made to FIG. 4C which illustrates a flow chart of a method of releasing gas using gas release mechanism 100, according to some exemplary embodiments of the present invention.

At 400, cover 108 is attached to fixation ring 110 and stomal cover 102 in factory. Optionally, stomal cover 102 is part of a new ostomy port 104. Alternatively, stomal cover 102 and ostomy port 104 are existing and are being retrofitted. Retrofit may be in factory or a retrofit agent.

At 401, the user introduces cap 106 through opening 122 in cover 108 (the cover was previously attached to fixation ring 110 at 400, prior to delivery to user), inserting tabs 134 through slots 126 until fitting the tabs in slots 120 in the fixation element.

At 402, cover 108 is rotated, optionally in a clockwise direction, for securely attaching cap 106 to fixation ring 110 and/or to stomal cover 102 and sealing proximal opening 114. Tabs 134 are pressed between rim 128 in cover 108 and slots 120 in the fixation element. Optionally, a thicker section 128A of rim 128 presses on tab 134. Alternatively, a thicker section of inclined surfaces 132 presses on tab 134. Optionally, a circumferential seal 138 around proximal opening 114 is pressed between circumferential wall 119 and a side wall 140 of cap 106 and seals proximal opening 114. In an exemplary embodiment of the invention, seal 138 is compressed to between 70-99% of its original thickness, for example 95%. Optionally, circumferential seal 138 is integrally formed as part of stomal cover 102. In an alternative embodiment, circumferential seal 138 may be a replaceable sealing element, for example an O-ring, fitted around proximal opening 114.

At 403, the user determines that gas release is required. Optionally, the user determines release based on experience following a period of time of day or following food consumption. Additionally or alternatively, a pressure sensing mechanism senses an increase in pressure inside the ostomy port and provides a visual and/or audible indication to the user. The indication may be a protruding element which may be seen and/or felt by the user, or an electrical or electromechanical indication such as, for example, a light, a vibration, and a sound.

At 404, the user rotates cover 108, optionally in a counter-clockwise direction (opposite direction from that in FIG. 4A). Rotation of cover 108 causes rim 128 to rotate so that thicker section 128A no longer presses tab 134 against slot 120, and is replaced by a thinner section 128B which does not press the tab against the slot.

At 405, optionally, cap 106 is displaced away from the proximal opening 114 by pressure from the gas inside ostomy port 104, separating side wall 140 from circumferential seal 138 and opening a gas flow path 142 to the ambient. Optionally, a separation between side wall 120 and circumferential bulge 138 ranges from 10 µm to 100 µm, 10 µm-70 µm, 10 µm-40 µm, 10 µm-30 µm, 10 µm-20 µm. Additionally or alternatively, cap 106 is manually displaced by the user. Optionally, the user may control the displacement of cap 106 by varying an amount of rotation of cover 108.

At 406, optionally, following gas release, return to 402 to close gas flow path 142 and seal proximal opening 114. Alternatively, go to 407 to release cap 106 from ostomy port 104.

At 407, rotate cover 102 in the counter-clockwise direction until tabs 134 are aligned with notches 126 and pulls cap 106 from opening 122 in the cover.

Figure 4E:
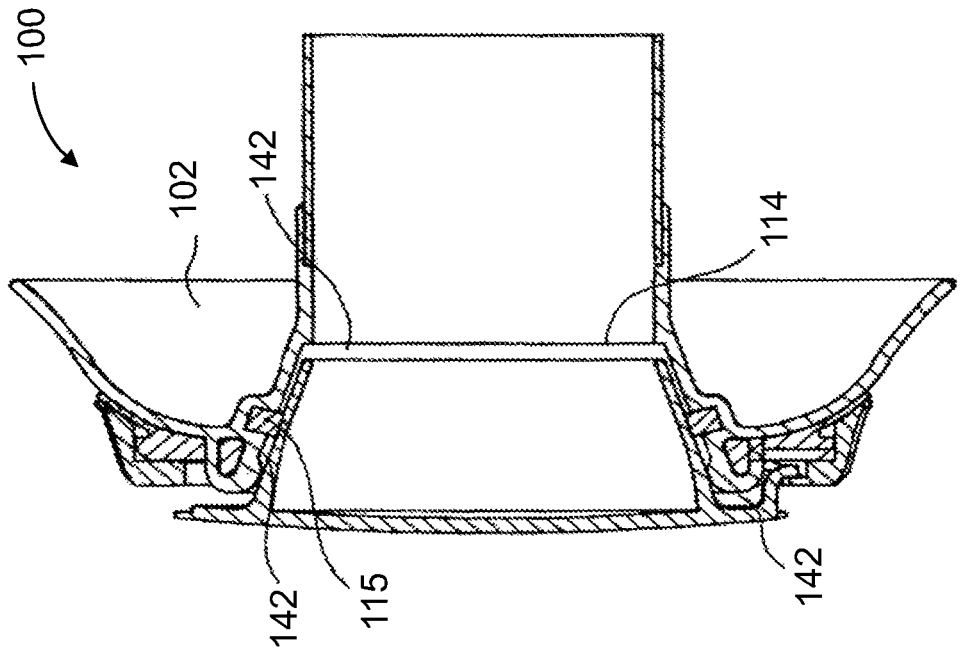
FIG. 4E schematically illustrates a sectional view of the gas release mechanism including the rotary cover and the filter in the ostomy port in the open gas flow path configuration, according to some embodiments of the present invention.
Figure 4D:
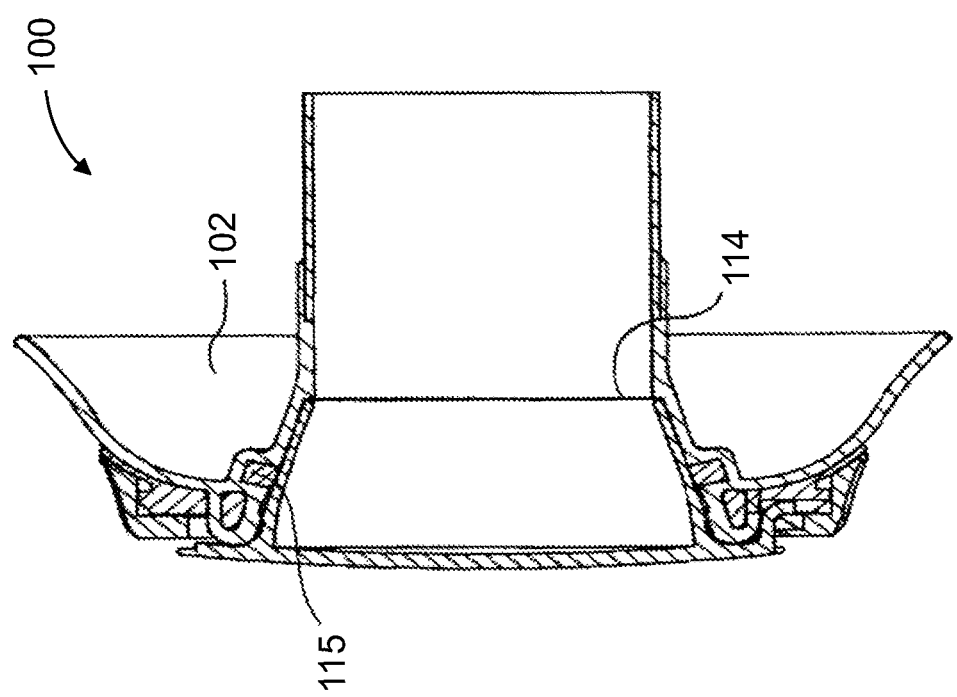
FIG. 4D schematically illustrates a sectional view of the gas release mechanism including the rotary cover and a filter in the ostomy port in the closed gas flow path configuration, according to some embodiments of the present invention.

Reference is now also made to FIGS. 4D and 4E which schematically illustrate sectional views of gas release mechanism 100 including a gas filter 115 in ostomy port 104, in the closed gas flow path configuration and the open gas flow path configuration, respectively, according to some embodiments of the present invention. In FIG. 4D, cap 106 seals proximal opening 114 for preventing waste contents and gas from escaping from ostomy port 104. In FIG. 4D, cap 106 is displaced away from proximal opening 114 for releasing gas from ostomy port 104 while preventing waste content from leaking out from the ostomy port.

In some exemplary embodiments, gas filter 115 is attached to stomal cover 102 so that it lies in gas flow path 142 when gas flow mechanism 100 is in the open gas flow path configuration for filtering the gas flowing therethrough to the ambient. Optionally, the filter is not in the flow and is not used up or contaminated when there is no gas flow.

In an exemplary embodiment of the invention, filter 115 is annularly shaped. Alternatively, filter 115 encircles only a portion of the circumference of the portion of ostomy port 104 to which it is attached. Optionally, filter 115 is stretchable, such that when cap 106 is pushed in the distal direction into ostomy port 104 (i.e. in the closed gas flow path configuration) filter 115 is stretched radially to accommodate cap 106. Additionally or alternatively, ostomy port 104 is deformable such that when cap 106 is pushed in the distal direction filter 115 is also pushed in the distal direction and ostomy port 104 is deformed to accommodate filter 115 in its altered position. When cap 106 is displaced away from proximal opening 114 (i.e. in the open gas flow path configuration), filter 115 resumes its original shape and position due to its own elasticity. Additionally or alternatively, filter 115 resumes its original shape and position due to the elasticity of the portion of ostomy port 104 to which it is attached.

In alternative embodiments (such as FIG. 7, below), a valve may be provided before the filter. In another embodiment, the valve and filter form an element which when moved either block flow along the lumen or allow flow through the filter. In one example, the filter is a cylinder with one half (lengthwise) being a blocking element and fits in a semi-annular portion of a lumen. In another example, the filter is pushed trans-axially into the lumen, to displace a blocking of the lumen. In another example, the filter lies in a kink in the lumen, which kink, when straightened allows gas flow through the lumen and the filter.

Optionally, filter 115 includes a charcoal filter element as known in the art. Alternatively, filter 115 may include any other filter element known in the art suitable for insertion into gas flow path 142. Filter 115 is replaceable and is optionally replaced each time the collection bag is replaced (or emptied in the case of reusable bags), for example, about 1-3 times a day. Filter replacement may require a higher frequency in case of loose and/or mixed content (e.g. in ileostomy) where the filter tends to get blocked.

Reference is now made to FIG. 5 which schematically illustrates an exemplary gas release mechanism 200 for attachment to a stomal cover 202 in an ostomy port 204, according to some embodiments of the present invention.

In some exemplary embodiments, gas release mechanism 200 includes a cover 208 having mechanical threads 224 and fixation ring 210 having matching mechanical threads 225. Optionally, fixation ring 210 is attached to stomal cover 202 using methods known in the art such as, for example, overmolding, welding, bonding, and the like. Alternatively, fixation ring 210 is formed together with, and as part of, stomal cover 202. Cover 208 is rotably attached to fixation ring 210 by mechanically screwing threads 224 onto threads 225. Optionally, cover 208 is a closed cover sealing an opening 212 in fixation ring 210 and a proximal opening (not shown) in ostomy port 204. Optionally, cover 208 and fixation ring 210 are substantially coaxially aligned with a center of the proximal opening. Alternatively, cover 208 includes an opening 222 for inserting a cap (not shown) through opening 212 for sealing ostomy port 104, the cap being functionally similar to cap 106. Additionally or alternatively, an ostomy bag (not shown) is attached to opening 222 for allowing waste content to flow out the proximal opening and through opening 222 into the bag.

In some exemplary embodiments, the user seals the proximal opening in ostomy port 204 for preventing escape of waste content and/or gas by screwing cover 208 onto fixation ring 210 and rotating the cover in a clockwise direction until the required sealing is obtained. For releasing gas, the user rotates cover 208 in a counter-clockwise direction until a notch 228 located on an upper section of fixation ring 210 and leading into opening 212 is exposed. Gas may then escape in an upward direction through notch 228 without leakage of waste content. Alternatively, fixation ring 210 does not include a notch and gas may escape through tiny spaces naturally existing between the threading when screwing cover 208 is not sufficiently fastened onto fixation ring 210. Alternatively, the user seals the proximal opening by rotating cover 208 in a counter-clockwise direction and opens the gas flow path by rotating the cover in the clockwise direction.

Reference is now made to FIG. 6 which schematically illustrates an exemplary gas release mechanism 300 for attachment to a stomal cover 302 in an ostomy port 304, according to some embodiments of the present invention.

In some exemplary embodiments, fixation ring 310 includes an elastically deformable circular opening 312 peripherally bordered by a circumferential rim 311. Fixation ring 310 is configured to sealingly accommodate a cap 306 for sealing a proximal opening (not shown) in ostomy port 304, preventing waste content and gas from escaping from ostomy port 304. Alternatively, the proximal opening is opening 312. Optionally, cap 306 is functionally similar to cap 106.

In some exemplary embodiments, for opening a gas flow path from ostomy port 304 to the ambient while cap 306 is inserted in deformable opening 312, the user laterally presses on circumferential rim 311. Optionally, lateral pressing may include pressing on circumferential rim 311 on two opposing sections along the circumference. Optionally, the two sections are radially opposed. Laterally pressing on circumferential rim 311 deforms circular opening 312 so that a gas flow path 342 is opened between cap 306 and the circumferential rim. Gas may then escape to the ambient while the waste content remains inside ostomy port 304. Upon removing the pressing action from circumferential rim 311, the elastically deformable opening 312 returns to its original shape so that the gas flow path between the circumferential rim and cap 306 is closed and neither waste content nor gas can escape from ostomy port 304.

Figure 7:
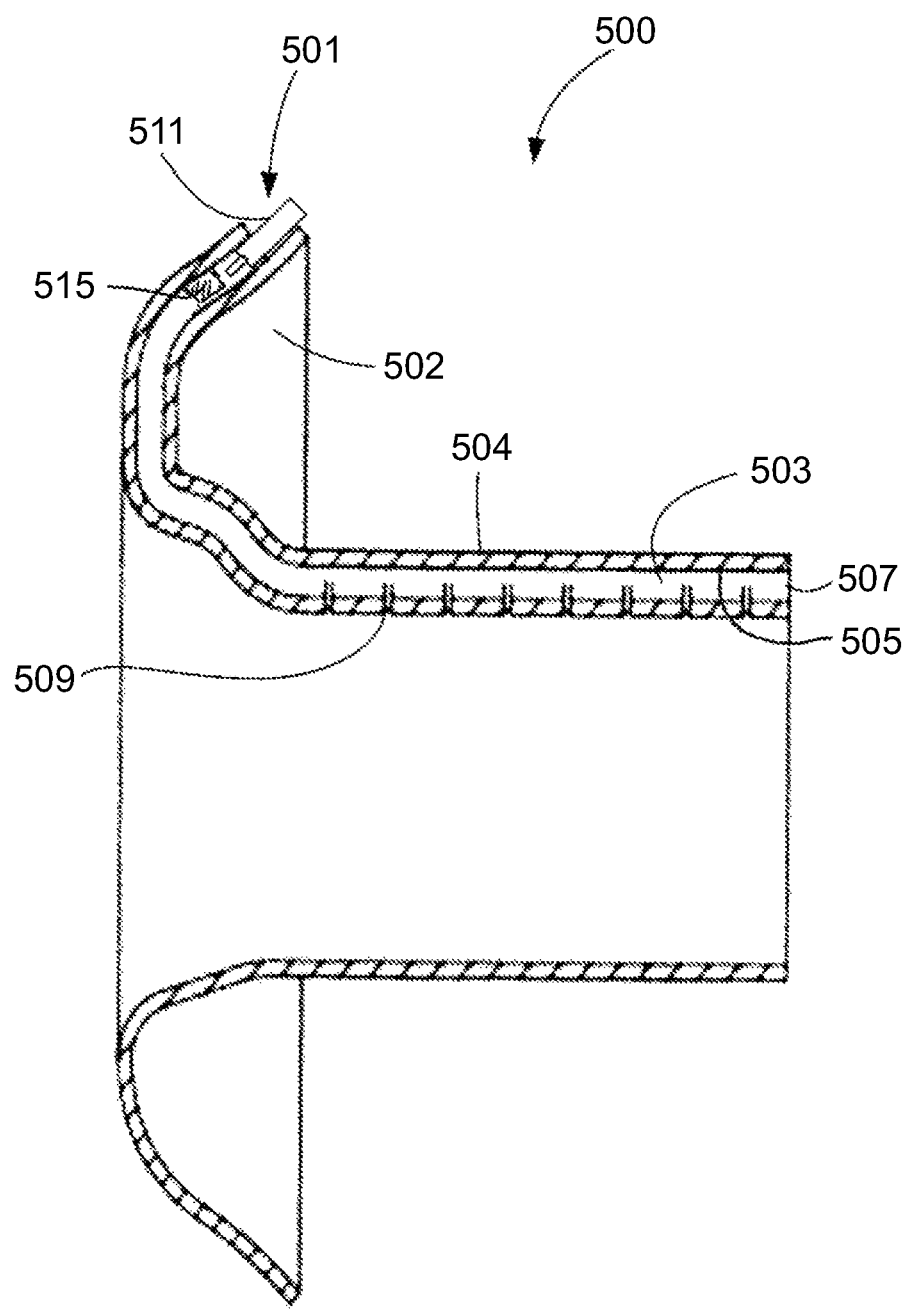
FIG. 7 schematically illustrates an exemplary gas release mechanism having a ventilation port and a lumen for use with an ostomy port having a stomal cover, according to some embodiments of the present invention.

Reference is now made to FIG. 7 which schematically illustrates an exemplary gas release mechanism 500 including a ventilation port 501 and a lumen 503 in an ostomy port 504, according to some embodiments of the present invention.

In some exemplary embodiments, ventilation port 501 is located on stomal cover 502 and connects to lumen 503 which extends along a length of an inner wall 505 of ostomy port 504. Optionally, lumen 503 may include a plurality of lumens extending along inner wall 505. Optionally, lumen 503 includes a distal opening 507 through which gas from ostomy port 504 enters through the lumen and flows in a direction of ventilation port 501 and out to the ambient. Additionally or alternatively, lumen 503 includes one or more lumen openings 509 along the length of the lumen through which gas enters into the lumen and flows to ventilation port 501. Optionally, lumen 503 is placed on an upper section of inner wall 505 for allowing rising gases to flow into the lumen while waste content remains on a bottom section of the inner wall. Optionally, ventilation port 501 is placed on an upper section of stomal cover 502 for allowing improved flow of the gases from lumen 503 to the ambient.

In some exemplary embodiments, a valve 511 is connected to ventilation port 501 for allowing the user to control releasing of gas into the ambient. Optionally, valve 511 is a stopcock. Alternatively, valve 511 is a Schrader valve or other type of valve known in the art and suitable for the application.

Referring to valve 511, various valve mechanisms may be used in this or other embodiments of the invention. In an exemplary embodiment of the invention, the valve is a mechanical valve which releases gas when a threshold pressure is passed. In an exemplary embodiment of the invention, the valve is an electronic valve comprising, for example, a pressure sensor, circuitry and an electronically actuated valve component.

In an exemplary embodiment of the invention, the valve generates an alert, for example, vibrating, popping up (e.g., mechanically) or sending a wireless message. Optionally, a transmitter and/or sound or light generator is provided.

In an exemplary embodiment of the invention, the user can select a valve or adjust a valve so as to set the threshold and/or gas release rate.

In an exemplary embodiment of the invention, when used in an airplane or elevator, such a valve can prevent or reduce discomfort caused by changes in ambient air pressure.

Reference is now also made to FIGS. 8A through 8G which schematically illustrate exemplary configurations for lumen 503 in FIG. 7, according to some embodiments of the present invention. The different configurations may provide for enhanced structural rigidity of the lumen for preventing their possible collapse and blocking of the lumen.

Figure 8A:
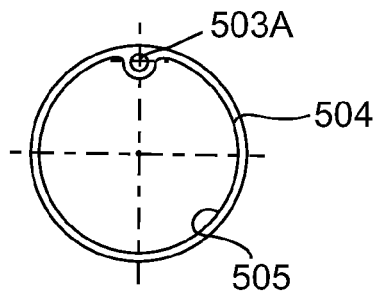
FIGS. 8A through 8G schematically illustrate exemplary configurations for the lumen, according to some embodiments of the present invention.
Figure 8B:
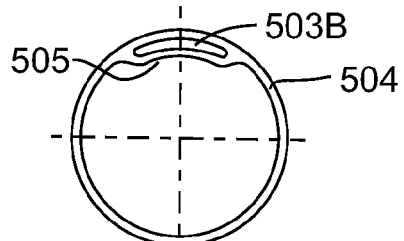
Figure 8C:
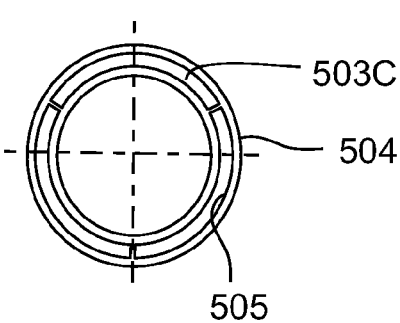
Figure 8D:
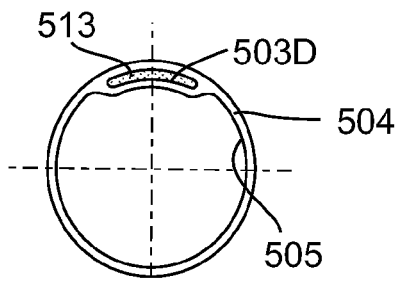
Figure 8E:
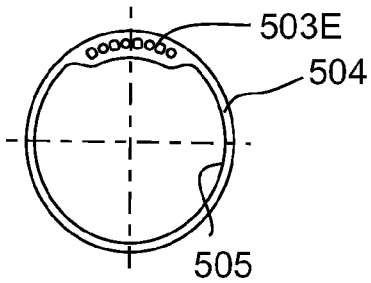
Figure 8F:
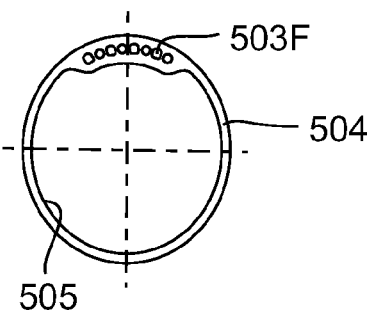
Figure 8G:
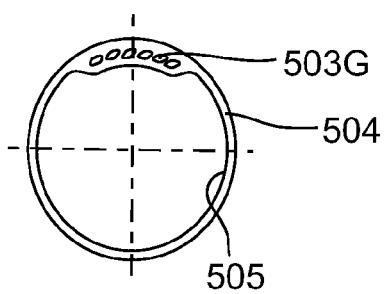

In some exemplary embodiments, lumen 503 has a circular cross-section, as per lumen 503A in FIG. 8A. Alternatively, lumen 503 has an elongated cross-section covering a larger portion of inner wall 505, as per lumen 503B in FIG. 8B. Alternatively, lumen 503 encircles all of inner wall 505, as per lumen 503C in FIG. 8C. Additionally or alternatively, lumen 503 is filled with open-cell foam 513, as per lumen 503D in FIG. 8D. Alternatively, lumen 503 includes a plurality of smaller lumens distributed over a larger portion of inner wall 505, as per lumen 503E in FIG. 8E, for improving a structural integrity of ostomy port 504. Optionally, lumen 503E in FIG. 8E can include different shaped smaller lumens, as per lumen 503F in FIG. 8F, and lumen 503G in FIG. 8G.

Figure 9:
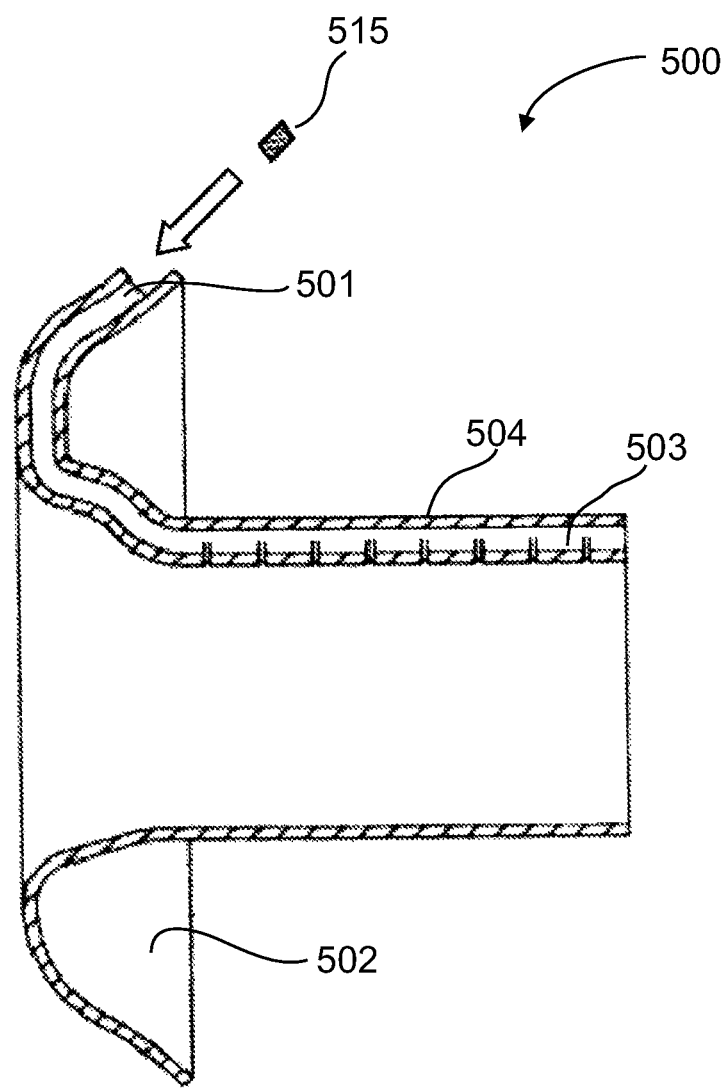
FIG. 9 schematically illustrates the gas release mechanism with a filter being inserted into the ventilation port, according to some exemplary embodiments of the present invention.

In some exemplary embodiments, replaceable gas filter 515 is insertable into ventilation port 501 for filtering the gas flowing through lumen 503 into the ventilation port prior to release into the ambient. Reference is made to FIG. 9 which schematically illustrates gas release mechanism 500 with filter 515 being inserted into ventilation port 501, according to some exemplary embodiments of the present invention.

Figure 10A:
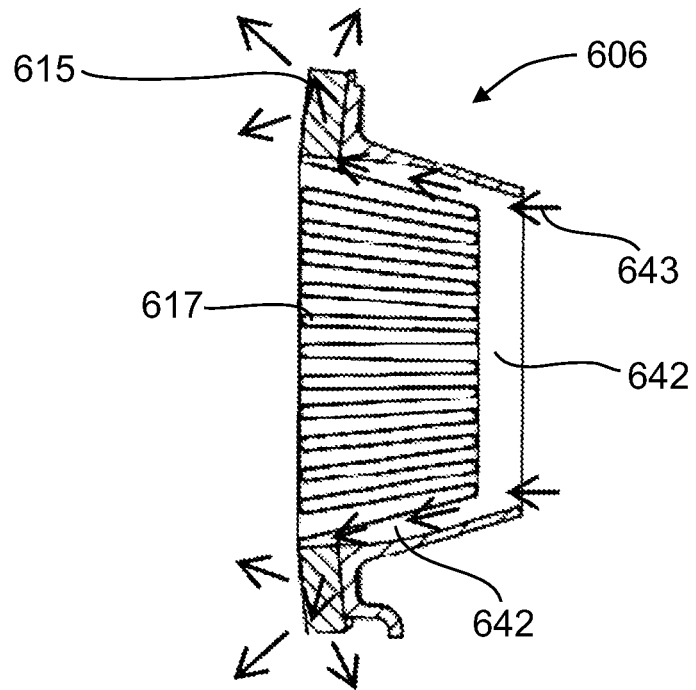
FIG. 10A schematically illustrates an exemplary cap with a waste content disposal bag and including a gas filter for use with an ostomy port, according to some embodiments of the present invention.
Figure 10B:
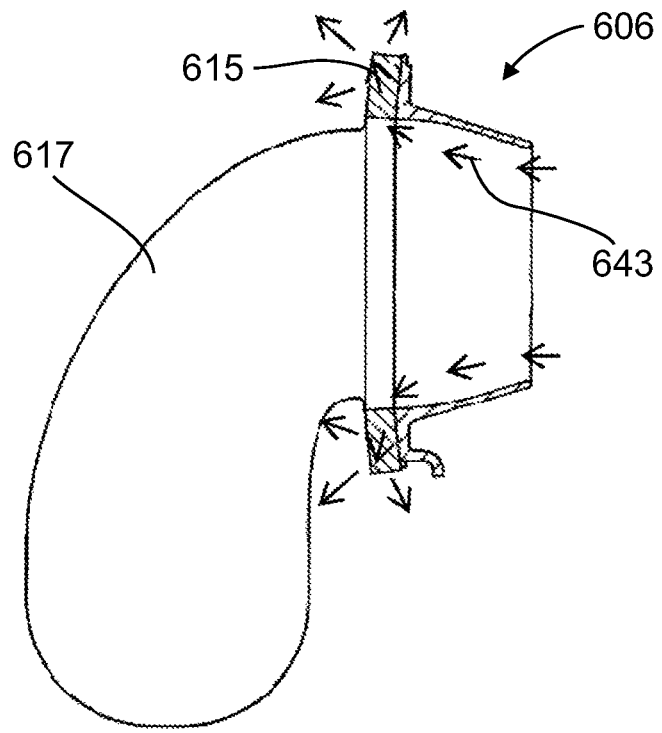
FIG. 10B schematically illustrates the cap following deployment of the waste content disposal bag, according to some embodiments of the present invention.

Reference is now made to FIGS. 10A and 10B which schematically illustrate an exemplary cap 606 with a waste content disposal bag 617 and including a gas filter 615 for use with an ostomy port (not shown), according to some embodiments of the present invention. Optionally, gas filter 615 includes a charcoal filter element. Alternatively, gas filter 615 includes any other filter element known in the art suitable for being used in cap 606.

While in one embodiment filter 515 and/or filter 615 comprises charcoal, other smell adsorbing materials may be used. Optionally or alternatively, filter 515 is configured to stop particles, for example, being a mesh or a tangle of threads, even if inert. Optionally or alternatively, filter 515 (or 615 or other filters) includes a stench negating function, for example, by smell release and/or by breaking down stench-causing molecules.

In some exemplary embodiments, cap 606 includes waste content disposable bag 617. Optionally, gas filter 615 is mounted on cap 606 so that it does not interfere with deployment of bag 617. Optionally, gas filter 615 includes an annular shape and is fitted around margins of cap 606. Optionally, cap 606 includes a gas flow path 642 around bag 617 directing gas 643 from the ostomy port to gas filter 615 and therefrom to the ambient. Optionally, gas filter 615 continues to filter gas 643 following deployment of bag 617.

A particular feature of some embodiments of the invention is that gas release can be applied independently of other uses of ostomy port, for example, without risk of becoming dirty (so out in open and not in bathroom), and/or as many times as needed (e.g., in case of gas generation or intestinal discomfort and/or disease.

Gas release can take, for example, between 1 second and five minutes. Optionally, the patient/user moves about to assist in gas exit. Exemplary release times are 1-2 minutes. In an exemplary embodiment of the invention, release is a daily occurrence, for example, being done 1-7 times a day, significantly more often than bag replacement or waste exit and/or at least 10 minutes before or after waste exit. Optionally, an extension tube (not shown), for example, between 3 and 50 cm long, is provided on the exit port to allow a user to aim the exit direction of the gas. Optionally, the tube includes a manual valve at it tip.

As it is a regular occurrence, gas may be periodically released for several days in a row, for example, 5, 10, 20 days or more over long periods of time, such as 1-6 weeks or more. Optionally, the circuitry is set to automatically release gas at certain times (e.g., during sleep) and/or periods and/or in response to motion detection (e.g., acceleration or lack thereof).

In some embodiments of the invention, kits are provided, generally in sterile packaging.

In an exemplary embodiment of the invention, components as described herein are sold in kit form. For example, an ostomy port may be sold with one or more caps and/or one or more filters or valves.

In another example, a retrofit coupling device may be sold, matched to a particular port and/or bag designs.

In another example, a set of replacement filters and/or replacement bags and/or caps may be packaged together, for example, as a package of 5, 10, 20 or smaller, intermediate or larger numbers.

Figure 11:
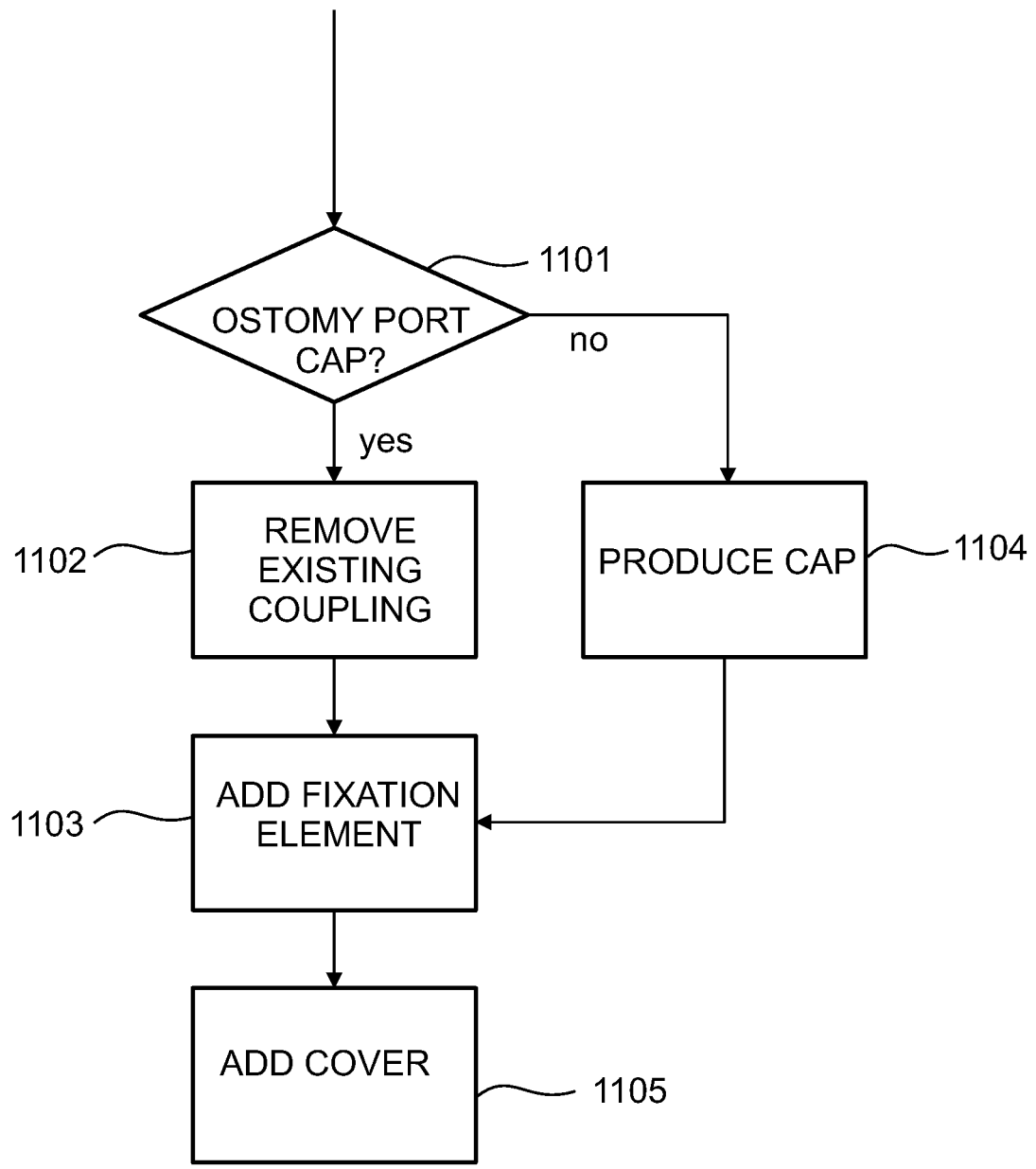
FIG. 11 is a flow chart illustrating a method of retrofitting an ostomy port with a gas release mechanism including a rotary cover and a fixation element, according to some embodiments of the present invention.

Reference is now made to FIG. 11 which is a flow chart illustrating a method of retrofitting an ostomy port with a gas release mechanism including a rotary cover and a fixation element, according to some embodiments of the present invention.

At 1101, a decision is made by the retrofitter as to whether or not the ostomy port includes a cap used for sealing a proximal opening in the port. Exemplary ports having caps are described in U.S. Pat. Nos. 4,121,589; 4,338,937; and 6,033,390. Exemplary ports not having caps are described in U.S. Patent Application Publication NO. 2010/0174253 and U.S. Pat. Nos. 4,662,890 and 5,569,216. If the port has a cap, go to 1102. Otherwise, go to 1104.

At 1102, remove any existing coupling mechanism between the ostomy port and the cap.

At 1103, add in a proximity to the proximal opening of the port a fixation element surrounding this opening. Go to 1105.

At 1104, produce a cap capable of sealingly closing the proximal opening of the ostomy port. Go to 1103.

At 1105, add a cover adapted to accommodate said cap and to rotate on said fixation element, such that rotation of the cover in one direction creates a sealing contact between the cap and the ostomy port, and rotation of the cover in the other direction loosens said sealing contact, thus creating a gas flow path from an interior of the ostomy port.

The terms "comprises", "comprising", "includes", "including", "having" and their conjugates mean "including but not limited to".

The term "consisting of means "including and limited to".

The term "consisting essentially of" means that the method or structure may include additional steps and/or parts, but only if the steps and/or parts do not materially alter the basic and novel characteristics of the claimed method or structure.

As used herein, the singular form "a", "an" and "the" include plural references unless the context clearly dictates otherwise.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of controlled gas release from an ostomy port having a deployable waste collection bag, comprising:
   determining that there is a need to release gas from a body of a patient; and
   releasing said gas from said body to an outside thereof through a gas release pathway that starts inside said body and passes through a gas release mechanism comprising at least one dedicated exhaust lumen configured to be selectively opened, while said waste collection bag remains undeployed, by opening said dedicated exhaust lumen;
   wherein said gas release pathway does not enter the interior of said waste collection bag, when deployed and when undeployed.

2. The method according to claim 1, wherein said determining comprises determining by an automatic mechanism.

3. The method according to claim 1, wherein said determining comprises determining by a human.

4. The method according to claim 1, wherein said determining comprises determining in response to a sensor.

5. The method according to claim 1, wherein said opening comprises opening a valve in said dedicated exhaust lumen.

6. The method according to claim 1, wherein said opening comprises opening a gap between said port and a seal thereof.

7. The method according to claim 1, wherein said pathway includes a stench negating material therein.

8. The method according to claim 1, wherein said pathway includes a filter therein.

9. The method according to claim 1, comprising repeating said determining and releasing at least two times in 24 hours, for at least 5 days in a period of 30 days; wherein said releasing is not performed while irrigating through said pathway.

10. The method according to claim 1 wherein said opening includes adjusting a release rate of said gas to between 1 ml/sec and 50 ml/sec.

11. An ostomy port providing control of gas release, comprising:
    a waste conduction channel terminating at a waste collection bag; and
    a gas release mechanism comprising at least one dedicated exhaust lumen and adapted to release gas passing from a body of a patient through a portion of said waste conduction channel and out through said dedicated exhaust lumen without said gas entering said waste collection bag, when deployed and when undeployed; wherein:
    said gas release mechanism is configured to be selectively open.

12. The port according to claim 11, wherein said channel is manually openable.

13. The port according to claim 11, wherein said gas release mechanism includes a gap between said channel and a body of said port.

14. The port according to claim 13, wherein said gas release mechanism comprises at least one distortable component which, when distorted, provides said gap.

15. The port according to claim 13, wherein said gas release mechanism comprises at least one movable element which, when moved, provides said gap.

16. The port according to claim 15, wherein said at least one movable element is configured to be moved in a plane perpendicular to an axis of said channel.

17. The port according to claim 11, wherein said gas release mechanism includes one dedicated lumen.

18. The port according to claim 11, wherein said gas release mechanism includes a plurality of lumens.

19. The port according to claim 17, wherein said gas release mechanism includes a plurality of openings into said channel.

20. The port according to claim 11, wherein said gas release mechanism includes a stench treating material.

21. The port according to claim 11, wherein said gas release mechanism includes a valve.

22. The port according to claim 21, wherein said gas release mechanism includes an automatically actuated valve.

23. The port according to claim 21, wherein said gas release mechanism includes a pressure sensor which generates a signal in response to a pressure level.

24. The ostomy port according to claim 11, wherein said gas release mechanism is integral to the port.

25. The port according to claim 24, wherein said gas release mechanism includes a filtering pathway.

26. The ostomy port according to claim 11, wherein said dedicated exhaust lumen does not empty into said bag.

27. The ostomy port according to claim 11, further comprising:
    a cap; and
    a coupling device configured to couple said cap to said port and to provide selective gas release.

28. The ostomy port according to claim 27, wherein said coupling device is adapted to rotate relative to said port and provide a gap for gas release from said port.

29. The ostomy port according to claim 28, wherein said coupling device is configured to be rotated a selected amount by a user, said selected amount determining the rate of gas release from said port.

30. The ostomy port according to claim 27, wherein said cap includes positioning elements and wherein said coupling device includes inclined surfaces, said positioning, elements and said inclined surfaces configured to sealingly lock said cap against said port.

31. The ostomy port according to claim 27, wherein said cap includes positioning elements and said coupling device includes inclined surfaces, said positioning elements and said inclined surfaces configured to create a gap between said cap and said port.

32. The ostomy port according to claim 31, wherein angular positioning of said inclined surfaces relative to said positioning elements determines a width of said gap.

33. The ostomy port according to claim 31, wherein said inclined surfaces are configured such that said gap is wider at a predetermined side of the gap.

34. The ostomy port according to claim 27, wherein said coupling, device is adapted to be distorted manually and provide a gap for gas release from, said port.

35. The method according to claim 1, wherein said ostomy port further comprises:

a cap; and a coupling device configured to couple said cap to the port and to provide filtered gas release.

36. The method according to claim 1, wherein said waste collection bag is attached or integral to said cap.

37. The method according to claim 2, wherein said manipulating said pathway comprises opening a valve in said dedicated exhaust lumen.

38. The method according to claim 3, wherein said manipulating said pathway comprises opening a valve in said dedicated exhaust lumen.

39. The method according to claim 4, wherein said manipulating said pathway comprises opening a valve, in said dedicated exhaust lumen.

40. The method according to claim 2, comprising repeating said determining and releasing at least two times in 24 hours, for at least 5 days in a period of 30 days; wherein said releasing is not performed while irrigating through said pathway.

41. The method according to claim 3, comprising repeating said determining and releasing at least two times in 24 hours, for at least 5 days in a period of 30 days; wherein said releasing is not performed while irrigating through said pathway.

42. The method according to claim 5, comprising repeating said determining and releasing at least two times in 24 hours, for at least 5 days in a period of 30 days; wherein said releasing is not performed while irrigating through said pathway.

43. The method according to claim 7, comprising repeating said determining and releasing at least two times in 24 hours, for at least 5 days in a period of 30 days; wherein said releasing is not performed while irrigating through said pathway.

44. The method of claim 1, wherein said gas is released such that gas passes from the stoma, along a portion of a waste conduction channel leading toward said waste collection bag, and out through said gas release pathway, without passing through the interior of said waste collection bag.

45. The method of claim 1, wherein said gas release mechanism is configurable from among at least two settings providing for different, non-zero release rates therethrough.

46. The ostomy port of claim 11, comprising: a gas release rate selector, operable to selectively open said gas pathway to one of at least two non-zero gas release settings.

47. The ostomy port of claim 11, wherein said waste collection bag is deployable from a cap of said ostomy port, and said dedicated exhaust lumen is operable while said waste collection bag remains undeployed.

48. A method of controlled gas release, from an ostomy port having a deployable waste collection bag, comprising:

providing a gas release pathway comprising a closed gas release mechanism comprising at least one dedicated exhaust lumen, wherein said dedicated exhaust lumen is configured to release gas through said port from a body of a patient when said lumen is open, opening said dedicated exhaust lumen from said body to an outside thereof while said waste collection bag remains undeployed;

wherein said gas pathway passes through said dedicated exhaust lumen and does not enter the interior of said waste collection bag, when deployed and when undeployed.

49. The method of claim 1, wherein said dedicated exhaust lumen is selectively open to the release of gas, and said releasing by manipulating comprises opening said dedicated exhaust lumen to allow release of gas.

50. The ostomy port of claim 11, wherein said dedicated exhaust lumen is configured to be selectively open to the release of gas.

* * * * *